United States Patent [19]
Inlow et al.

[11] Patent Number: 6,048,728
[45] Date of Patent: Apr. 11, 2000

[54] CELL CULTURE MEDIUM FOR ENHANCED CELL GROWTH, CULTURE LONGEVITY, AND PRODUCT EXPRESSION

[75] Inventors: Duane Inlow; Brian Maiorella, both of Oakland; William Howarth, Castro Valley, all of Calif.

[73] Assignee: Chiron Corporation, Emeryville, Calif.

[21] Appl. No.: 08/480,508

[22] Filed: Jun. 7, 1995

Related U.S. Application Data

[63] Continuation of application No. 08/379,027, Jan. 27, 1995, abandoned, which is a continuation of application No. 07/716,959, Jun. 18, 1991, abandoned, which is a continuation-in-part of application No. 07/248,634, Sep. 23, 1988, abandoned.

[51] Int. Cl.$^7$ .................................................... C12N 5/00
[52] U.S. Cl. ........................ 435/404; 435/325; 435/375
[58] Field of Search ............... 435/240.1, 240.2, 435/240.3, 240.31, 240.25, 240.27, 325, 375, 404

[56] References Cited

U.S. PATENT DOCUMENTS

| | | |
|---|---|---|
| 4,560,655 | 12/1985 | Baker . |
| 4,657,866 | 4/1987 | Kumar . |
| 4,816,401 | 3/1989 | Taupier et al. ........................... 435/325 |
| 4,879,222 | 11/1989 | Alderman et al. ....................... 435/325 |
| 5,122,469 | 6/1992 | Mather et al. ........................... 435/325 |
| 5,232,848 | 8/1993 | Wolfe et al. ............................. 435/325 |

FOREIGN PATENT DOCUMENTS

| | | |
|---|---|---|
| B-0 229 809 | 7/1987 | European Pat. Off. . |
| A-0 249 557 | 12/1987 | European Pat. Off. . |
| 2196348 | 4/1988 | United Kingdom . |
| 8700195 | 1/1987 | WIPO . |

OTHER PUBLICATIONS

Bettger et al, Proc. Natl. Acad. Sci. USA, vol. 78, No. 9, pp. 5588–5592, 1981.

Ill et al, In Vitro Cell & Dev. Biol., vol. 24, No. 5, pp. 413–419, May 1988.

Kovar et al., "Serum–free Medium For Hybridoma And Parental Mueloma Cell Cultivation: A Novel Composition Of Growth–Supporting Substances", *Immunol. Letters* 7:339–345 (1984).

Luan et al., "Strategies to Extend Longevity of Hybridomas in Culture and Promote Yield of Monoclonal Angtodies", *Biotechnol. Letters* 9:691–696 (1987).

Murakami et al., "Growth of hybridoma cells in serum–free medium: Ethanolamine is an essential component", *Proc. Natl. Acad. Sci.* (*USA*) 79:1158–1162 (1982).

Murakami, H., "Serum–Free Media Used for Cultivation of Hybridomas", in Monoclonal Antibodies: Production and Application 107–141 (Alan R. Liss, Inc. 1989).

Murakami et al., "Development of a Basal Medium for Serum–Free Cultivation of Hybridoma Cells in High Density", *Nippon Nôgeikagaku Kaishi* 58:575–583 (1984).

Murakami et al., "Development of a basal medium for serum–free cultivation of hybridoma cells in high density", *Chem. Abst.* 101:71010t (1984).

European Search Report (EP–B–0 435 911).

Notice of Opposition to a European Patent (EP–B–0 435 911).

English translation of Murakami et al., "Development of a Basal Medium for Serum–Free Cultivation of Hybridoma Cells in High Density", *Nippon Nôgeikagaku Kaishi* 58:575–583 (1984) (14 pages; translated by Okada & Sellin Translations).

Another English translation of Murakami et al., "Development of a Basal Medium for Serum–Free Cultivation of Hybridoma Cells in High Density", *Nippon Nôgeikagaku Kaishi* 58:575–583 (1984) (18 pages).

*Primary Examiner*—Leon B. Lankford, Jr.
*Attorney, Agent, or Firm*—Marshall, O'Toole, Gerstein, Murray & Borun; Kimberlin L. Morley; Robert P. Blackburn

[57] ABSTRACT

Protein-free cell culture media supplements are described consisting of synergistic combinations of medium components, which when added to cell culture media, either serum supplemented or serum-free, enhance cell growth, culture longevity and product expression.

39 Claims, 10 Drawing Sheets

6,048,728

CELL CULTURE MEDIUM FOR ENHANCED CELL GROWTH, CULTURE LONGEVITY, AND PRODUCT EXPRESSION

The present invention is a file wrapper continuation of U.S. Ser. No. 08/379,027, filed Jan. 27, 1995, now abandoned, which is a file wrapper continuation of U.S. Ser. No. 07/716,959, filed Jun. 18, 1991, now abandoned, which is a file wrapper continuation-in-part of U.S. Ser. No. 07/248,634, filed Sep. 23, 1988, now abandoned.

FIELD OF THE INVENTION

This invention is in the general field of animal cell culture. More particularly, the invention concerns improved media for the cultivation of animal cells and the production of natural and recombinant products derived therefrom.

BACKGROUND OF THE INVENTION

To date, efforts have been undertaken to develop culture conditions to maximize cell culture growth and thereby increase resultant product yield. Early work in the development of animal cell culture media focused on the formulation of such media to achieve rapid cell proliferation (White, P. R., 1946, *Growth,* 10:231–289, and Waymouth, C., 1974, *J. Natl. Cancer Inst.,* 53:1443–1448). Such media incorporate specific nutrients especially sugars, amino acids, vitamins, salts, and in some cases trace metal ions, purines, and pyrimidines. These media are most often supplemented with animal serum. Today some of the more widely used basal media for mammalian cell cultures include Hams F-12, Dulbecco's modified Eagle's medium (DME), RPMI 1640, and Iscove's modified DME.

Production of human monoclonal antibodies using hybridoma cell lines will be used in this application as an example for product expression in cell culture.

Culture media have been previously described which were developed specifically for low serum and serum-free mammalian cell cultures for production of monoclonal antibodies. One such serum-free medium is disclosed in European Patent Publication 076,647, published Apr. 13, 1983. Other media have been developed by changing levels of supplements such as trace elements, and vitamins and incorporating purified protein hormone additives. References to such media include, for example, Barnes, D., et al., 1980 *Cell,* 22:649–655; Cleveland, W. L., et al., 1983, *J. Immunol. Meth.,* 56:221–234; Iscove, N., et al., 1978, *J. Exp. Med.,* 147:923–933; Kawamoto, T., et al., 1983, *Analytical Biochemistry,* 130:445–453; Kovar, J., et al., 1986, *Immunology Letters,* 7:339–345; Murakami, H., et al., 1983, *Argic. Biol. Chem.,* 47(8):1835–1840; Murakami, H., et al., 1982, *Proc. Natl. Acad. Sci. USA,* 79:1158–1162; Muzik, H., et al., 1982, *In Vitro,* 18:515–524; and Wolpe, S. D., "In Vitro Immunization and Growth of Hybridomas in Serum-Free Medium", in J. P. Mather, ed., *Mammalian Cell Culture,* Plenum Press, New York, 1984; Hagiwara, H., et al., 1985, 117–122 in H. Murakami et al. (eds) Growth and Differentiation of Cells in Defined Environment, Springer-Verlag, Berlin, 1985; Tharakan, J. P., et al., 1986, *J. Immunol. Meth.,* 94:225–235; Cole, S.P.C., 1987, *J. Immunol. Meth.,* 97:29–35; McHugh, Y. E., 1983, *BioTechniques,* June/July issue:72–77. Components which are common to most if not all these media include glucose at concentrations up to 4.5 g/L, glutamine at concentrations of 2–4 mM, choline generally at about 1–4 mg/L, tryptophan and other amino acids. Tryptophan is generally present at concentrations less than 20 mg/L. Several of these media also contain the growth factors insulin and transferrin.

Efforts to increase antibody yield have focused primarily on means to optimize cell growth and cell density. As a general point of reference, antibody titres from murine hybridoma cell lines are highly variable from cell line to cell line and range typically from 10 to 350 mg/L (Lambert, K. J., et al., 1987, *Dev. Indust. Microbiol,* 27:101–106). Human monoclonal antibody expression from human/human or human/mouse fusions are also highly variable from cell line to cell line and range typically from 0.1 to 25 mg/L (Hubbard, R., *Topics in Enzyme and Fermentation Biotechnology,* Chapt. 7:196–263, Wisemand, A., ed., John Wiley & Sons, New York (1983). These values are indicative of culture conditions that are optimized for cell growth.

Another approach from the literature to increasing product production is to achieve high cell densities by cell recycle or entrapment methods. Examples of these methods include hollow fiber reactors (Altshuler, G. L., et al., 1986, *Biotech. Bioeng., XXVIII*:646–658; ceramic matrix reactors (Marcipar, A., et al., 1983, *Annals. N.Y. Acad. Sci.,* 413:416–420; *Nature,* 302:629–630); perfusion reactors (Feder, J., et al., 1985, *American Biotech. Laboratory,* III:24–36) and others.

While a variety of methods to increase product expression from cell culture are being explored, the primary focus is still on the optimization of cell growth. In typical culture media the culture dies rapidly after maximum cell density is reached.

Another example form the literature documents that, at least for some cell lines, product (monoclonal antibody) production proceeds even after a culture stops growing (Velez, D., et al., 1986, *J. Immunol. Meth.,* 86:45–52; Reuveny, S., et al., 1986, ibid at 53–59). Arathoon, W., et al., 1986, *Science,* 232:1390–1395 reported that a 1,000 liter hybridoma fermentation produced about 80 grams of monoclonal antibody during the growth phase and another 170 grams of antibody during an extended stationary/death phase. J. Birth, et al., (European Patent Application No. 87/00195, 1987) describe a procedure of Fed-batch culture wherein nutrients are added to a culture over time and culture longevity is increased. Final antibody titres from the culture are thus increased.

Thus, it will be appreciated that there is a critical need for media that will support the growth of animal cells and stimulate the production of products, including antibodies, and other natural or recombinant protein products to greater levels than can be realized using media that are currently available.

SUMMARY OF THE INVENTION

Accordingly, the invention presented herein describes a protein-free supplement (the "Primary Supplement"), which when added to standard cell culture media, enhances cell growth, culture longevity and product expression. Examples are given showing that this supplement is particularly effective in production of antibodies using hybridoma cell lines in serum-free culture, where final antibody titre is increased in one example from 80 mg/L to over 250 mg/L. The Primary Supplement is a hitherto unrecognized synergistic combination of standard medium components which are beneficial when added in the prescribed combination, and consists of 1) glutamine, 2) phospholipid precursors, including minimally both choline and ethanolamine, 3) tryptophan, and 4) additional amino acids as required for a particular cell line and product to be produced. When added individually, to standard media, these components have little effect, but are extremely effective when added together in the prescribed combination, and the deletion of any of the prescribed components diminishes the desired effect. Several of the components in the Primary Supplement are added to concentrations hitherto considered to be unnecessary or inhibitory. When added together in the prescribed combination, the supplement enhances cell growth, increases culture longevity by maintaining cells in a pseudo-stationary phase wherein product expression continues, and thus results in a significant increase in final product titre.

A second aspect of the invention is a description of several additional components, (the "Class I reagents"), which when added individually, or in various combinations to the Primary Supplement result in a further improvement to culture growth and/or product expression. Included in this class of additional components are reducing agents, trace metal ions, and/or vitamins.

A third aspect of the invention is the formulation of protein-free, serum-free and serum supplemented media containing the supplement, as well as in media supplemented with lipids and can be used with the addition of agents to induce solute stress.

A further aspect of the invention is a method of growing cells employing the media supplements described herein such that they can be included in medium at the start of culture, or can be added in a fed-batch or in a continuous manner. The resulting media can be used in various cultivation methods including, but not limited to, batch, fed-batch, chemostat and perfusion, and with various cell culture hardware including, but not limited to, stationary flasks, agitated flasks, spinner flasks, stirred fermentors, airlift fermentors, membrane reactors (including hollow fiber, flat membrane plate, external loop perfusion), reactor s with cells retained on a solid support or immobilized/entrapped as in microporous beads, and any other configuration appropriate for the growth or maintenance of the desired cell line.

DETAILED DESCRIPTION OF THE INVENTION

Figure 1:
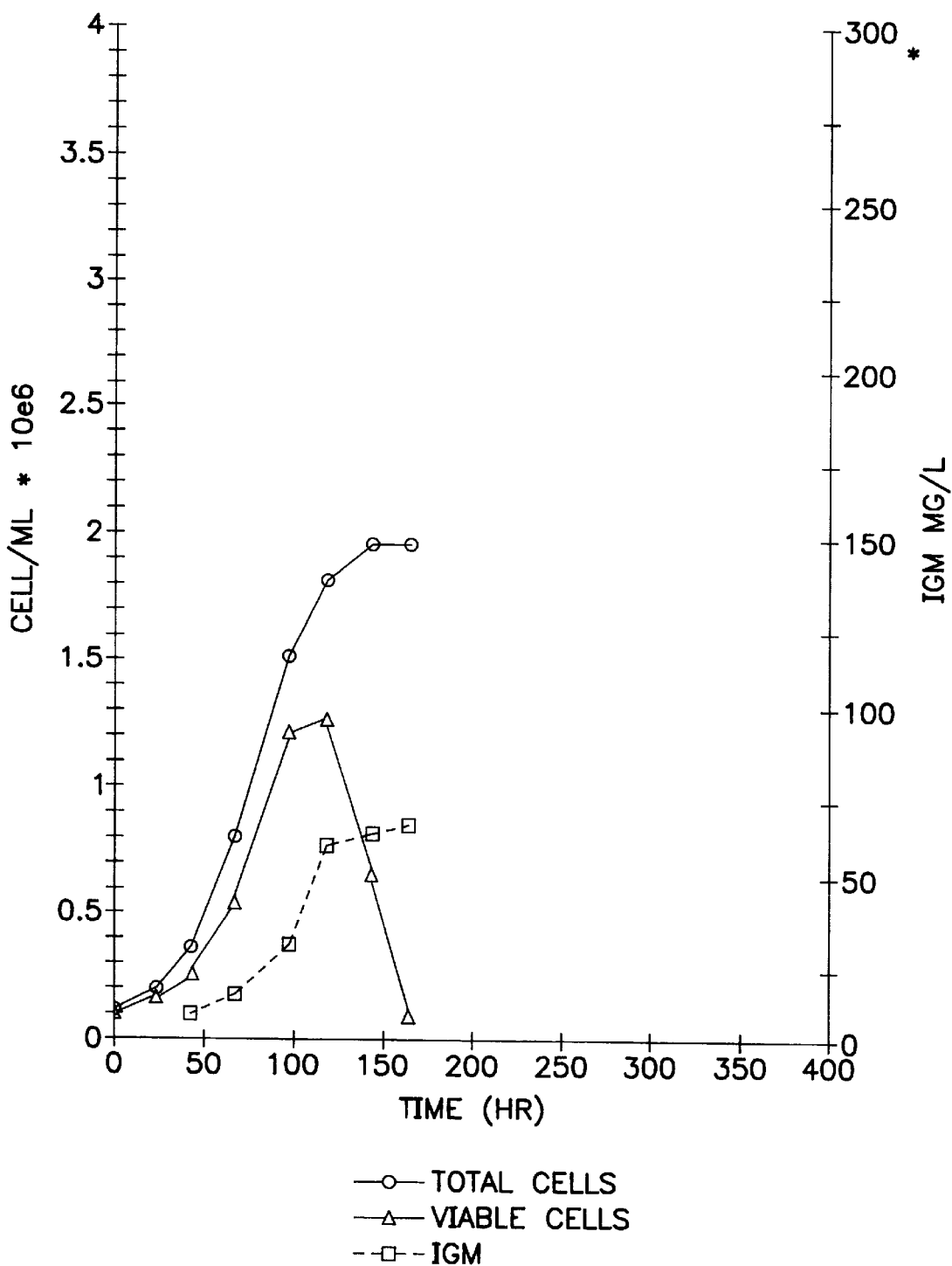
FIG. 1 shows the growth properties and levels of antibody produced by D234 in a typical commercially available medium, Ventrex HL-1.

The following reference is referred to throughout this application, and is presented here for the convenience of the reader. Ian Freshney (Culture of Animal Cells—A Manual of Basic Technique, Alan R. Liss, NY, 1987) tabulates compositions of typical basal media for use with serum (Table 7.5:74–75) and typical serum-free media compositions (Table 7.6:76–78) described in the literature for culture of a wide range of animal cells and expression of products therefrom. These tables are incorporated by reference.

The invention described herein is first concerned with a protein-free supplement compatible with standard cell culture media to enhance cell growth, culture longevity and product expression. The Primary Supplement is favored, and has advantages that arise, at least in part, by a hitherto unrecognized synergistic interaction of the reagents employed. Iscove (N. N. Iscove, Culture of Lymphocytes and Hemopoietic Cells in Serum-Free Medium:169–185 in Methods for Serum-Free Culture of Neuronal and Lymphoid Cells) describes the standard method for optimizing cell culture media wherein "the effect of individually doubling and quadrupling the concentration of each component was examined . . . ". This approach has been widely used in the cell culture field, which fails to recognize the possibility that components may act synergistically and that it may be necessary to combine supplements of several components to see a desired effect.

Components selected from a second group of cell culture reagents (the Class I reagents) when combined with the Primary Supplement can synergize to produce a more favorable cell culture supplement having especially beneficial effects on cells grown to high densities.

Before a detailed description of the classes of reagents is presented, and the media supplements that can be formulated therefrom, a brief definition of some of the technical terms used throughout this application will facilitate understanding the nature of the invention.

I. Definitions

"Basal medium" is defined herein to include a nutrient mixture of inorganic salts, sugars, amino acids, and, optionally, vitamins, organic acids and/or buffers or other well known cell culture nutrients. These reagents are necessary to support cell growth and reproduction. The preferred basal media which is a component of the instant cell growth media compositions contains neither serum, nor proteins. A wide variety of commercially available basal media are well known to those skilled in the art, and include Dulbeccos' Modified Eagles Medium (DMEM), Roswell Park Memorial Institute Medium (RPMI), Iscove modified Dulbeccos' medium and Hams medium.

The amino acid concentration (in mg/L) of Dulbecco's Modified Eagle's Medium (DMEM) is: L-Arginine.HCl=84; L-Cysteine.2HCl=62.57; L-Glutamine=584; Glycine=30; L-Histidine.HCl.H$_2$O=42; L-Isoleucine=104.8; L-Leucine= 104.8; L-Lysine.HCl=146.2; L-Methionine=30; L-Phenylalanine=66; L-Serine=42; L-Threonine=95.2; L-Trptophan=16; and L-Tyrosine disodium salt.H$_2$O=103.8. The amino acid concentration (in mg/L) of Roswell Park Memorial Institute Medium (RPMI) 1640 medium is L-Arginine=200; L-Asparagine.H2O=56.82; L-Aspartic acid=20; L-Cysteine.2HCl=65.2; L-Glutamic acid=20; L-Glutamine=300; Glutathione=1; Glycine=10; L-Histidine=15; L-Hydroxyproline=20 L-Isoleucine=50; L-Leucine=50; L-Lysine.HCl=40; L-Methionine=15; L-Phenylalanine=15; L-Proline=20; L-Serine=30; L-Threonine=20; L-Trptophan=5; L-Tyrosine disodium salt.$H_2O$=28.83; and L-Valine=20.

The term "hybridoma", refers to a hybrid cell line produced by the fusion of an immortal cell line of immunologic origin, and an antibody producing cell. The term is meant to include progeny of heterohybrid myeloma fusions, which are the result of a fusion with human cells and a murine myeloma cell line subsequently fused with a plasma cell, referred to in the art as a trioma cell line. Additionally, the term is meant to encompass virtually any immortalized hybrid cell line which produced antibody such as, for example, quadromas. Milstein, C., et al., 1983, *Nature*, 537:3053. Moreover, the hybrid cell lines can be of virtually any species, including human and mouse.

The term "microemulsion" refers to a lipid mixture emulsified substantially without the aid of proteinaceous materials such as those found in serum, particularly serum albumin. Generally, emulsifiers described in U.S. patent application Ser. No. 077,189 will be employed to form the microemulsion. This patent application is hereby incorporated by reference in its entirety. Generally, pluronic polyols are favored as the emulsifier.

As used herein the phrase "solute stress" refers to the addition of solutes in such concentrations that produce a growth inhibitory effect or reduced final cell density, that is, a growth rate or maximum cell density less than that determined for optimal growth. However, the level of product expressed at this reduced growth level is comparatively greater than that level of expression achieved at the optimal growth rate owing to an increase in specific (per cell) product expression rate or an increase in longevity of the culture. Generally, solutes and methods described in U.S. patent application, Ser. No. 122,015 will be employed. This application is hereby incorporated by reference in its entirety.

"Pseudo-Stationary phase" refers to a period of culture growth occurring after the exponential growth phase and wherein the rates of cell growth and death are similar such that the viable cell concentration changes only relatively slowly with time (as compared to during the exponential growth or the death phase).

"Cell growth hormones" or "growth factors" is meant to encompass a large number of molecules either naturally occurring or genetically engineered, as well as fragments, derivatives or modifications thereof, that stimulate the growth, or supports the maintenance of cells in defined media. Examples of the former includes transferrin and insulin, among others. Examples of growth factors includes nerve growth factor, epidermal growth factor, fibroblast growth factor, and endothelial cell growth factor, among others. It is important to note that different animal cell lines may vary in their requirements for one or more of these molecules, and that the optimal hormones or growth factors, or a mixture of the same, is readily determined using standard cell culture techniques.

As used herein the phrase "Fed-Batch" defines a method of supplying the compositions of the instant invention to cells such that the concentration of a reagent is additive of the individual additions of the reagent.

The instant invention presents cell culture media supplements that are compatible with the general growth and maintenance requirements of animal (especially mammalian) cells in vitro, and particularly enhances or supports the expression of differentiated properties associated with specific cell types, for example, an elevated production of monoclonal antibodies by hybridoma cell lines. Thus, it will be appreciated that the instant supplements have widespread applications, being generally useful for routine culture of cells, as well as being employed in those instances when great amounts of a natural or recombinant cellular product is desired that is produced by cells in culture.

II. Primary Supplement

The Primary Supplement of the current invention consist of a class of reagents that includes, in combination, 1) glutamine, 2) phospholipid precursors including preferably choline and ethanolamine, 3) tryptophan, and 4) additional amino acids as required for the particular cells lines.

A. Glutamine

In the Primary Supplement, glutamine is included at over 5 mM, and preferably at 8–20 mM. However, in Fed-Batch mode glutamine may be as high as 40 mM. It is important to note that these concentrations are significantly above those typically found in cell culture media.

Glutamine is recognized as both an amino acid building block for protein synthesis and as a primary energy source in cell culture (W. L. McKeehan, Glycolysis, Glutaminolysis and Cell Proliferation, *Cell Biology Intro. Reports,* 1982, 6(7):635–650, L. J. Reitzer, et al, Evidence that Glutamine, Not Sugar, Is the Major Energy Source for Cultured HeLa Cells, *J. Biological Chemistry,* 1979, 254(B):2669–2676, H. R. Zielke, et al., Reciprocal Regulation of Glucose and Glutamine Utilization by Cultured Human Diploid Fibroblasts, *J. Cell Physiol.,* 1978, 95:41–48.

Reference to the summary of typical media compositions tabulated in Freshney, above, shows that glutamine is typically included at 2 or 4 mM in standard serum-supplemented and serum-free medium formulations. In contrast, as mentioned above, the composition of the instant invention contains elevated amounts of glutamine above 5 mM, and preferably about 8–20 mM.

Both glutamine metabolism as well as spontaneous decomposition of glutamine (G. L. Trisch, et al., Spontaneous Decomposition of Glutamine in Cell Culture Media, *Experimental Cell Research,* 1962, 28:360–364) result in the release of ammonium ion which is widely described in the literature as toxic to either cell growth or protein production (S. Reuveny, et al., Factors Affecting Cell Growth and Monoclonal Antibody Production in Stirred Reactors, *J. Immunl. Methods,* 1986, 86:53–59, and some researchers have argued that glutamine when added at high concentrations will have a toxic effect (indirectly through increased production of ammonium ion). Some researchers have advocated minimizing the concentration of glutamine present in the culture by adapting the culture to grow in the absence of glutamine and with glutamic acid as an alternate substrate (J. B. Griffiths, et al., The Uptake of Amino Acids by Mouse Cells During Growth in Batch Culture and Hemostat Culture, The Influence of Cell Growth Rate, *Proc. Roy Soc. B.,* 1967, 168:421–438), or by utilizing slow addition of glutamine throughout the time course of the culture to maintain a relatively constant low concentration of glutamine (M. W. Glacken, et al., Reduction of Waste Product Excretion via Nutrient Control: Possible Strategies for Maximizing Product and Cell Yields on Serum in Cultures of Mammalian Cells, *Biotechnol. Bioeng.,* 1986, 28:1376–1389).

Based on the forgoing discussion, it will be realized that for cell lines which have been adapted to grow with glutamate or asparagine or other substitute for glutamine, that the methods of the current invention are still applicable, except that elevated levels of glutamate or other substitute would be included in the supplement in place of glutamine. For cell lines that have been adapted to grow with low concentrations of glutamine maintained by glutamine addition throughout the culture, the methods of the current invention are also applicable except that the increased quantity of glutamine will be added gradually over the course of the culture.

Recently, some researchers have found that addition of supplemental glutamine late in culture can increase culture longevity for some cell lines (S. Reuveny, et al., Factors Affecting Cell Growth and Monoclonal Antibody Production in Stirred Reactors, *J. Immunol. Methods,* 1986, 86:53–590).

We have found that supplemental glutamine can be added either at the start of culture, or during the course of culture with the total of glutamine added to about 5–40 mmoles and preferably about 8–20 mmoles per liter. We believe that late in culture, in a post exponential growth pseudo-stationary phase, that glutamine can be a major energy source for the cells, (i.e. glutamine consumption continues while glucose consumption may decline). We find that glutamine supplementation is necessary, but not sufficient to achieve the desired increase in culture longevity. To achieve the optimal performance, glutamine must be added in combination with the other reagents of the Primary Supplement.

B. Phospholipid Precursors

The Primary Supplement also contains phospholipid precursors, selected from the group including but not limited to, serine, inositol, choline, ethanolamine, and glycerol. While these components are all phospholipid precursors, they also have other biochemical roles, and this invention should not be considered as being limited by any proposed hypothesis of a mechanism of action.

Serine is considered an essential amino acid, and inositol an essential vitamin. Most cell culture media contain serine and inositol at adequate levels for their roles as phospholipid precursors and other biochemical roles.

Choline is included as a vitamin in most media at 1–4 mg/L. However, on occasion, choline has been used at higher concentrations. For instance, to grow cells of non-lymphoid origin, Ham (R. G. Ham, Clonal Growth of Mammalian Cells in a Chemically Defined Synthetic Medium, *Proc. Natl. Acad. Sci. USA,* 1965, 53:288–293) includes choline at 15 mg/L in a serum-free medium for clonal growth of Chinese Hamster Ovary Cells. J.Birch, et al., *J. Cell Sci.,* 1969, 5:135–142) includes choline at 20 mg/L in a serum containing medium for growth of mouse fibroblasts. Waymouth's (C. Waymouth, Rapid Proliferation of Sublines of NCTC Clone 929 Mouse Cells in a Simple Chemically Defined Medium, *J. Natl. Cancer Inst.,* 1959, 22:1003–1017) medium MB 752/1 for culture of mouse L929 fibroblast connective tissue cell line is exceptional in including choline at 250 mg/L. Although Ham, Birch and Waymouth developed media to support cell growth, they did not study the production of biological products produced by cells grown in the media. We have found that cells, preferably antibody secreting cells, grow and secrete maximal amounts of antibody in media containing choline supplemented to a level of greater than about 4 mg/L, and preferably at approximately 4–75 mg/L in combination with the other reagents of the Primary Supplement. At these concentrations, choline does not become limiting and is without apparent toxicity.

Ethanolamine is not typically included in serum supplemented media. Murakami (H. Murakami, et al., *Proc. Natl. Acad. Sci. USA,* 1982, 79:1158–1162) demonstrates that ethanolamine at 20 uM is stimulatory to growth of a murine hybridoma cell line. Tharakan, et al., *J. Immunol. Methods,* 1986, 94:225–235; Cole, et al., *J. Immunol. Methods,* 1987, 97:29–35; and Kovar, et al., *Immunol. Letters,* 1984, 7:339–345 also found ethanolamine to be stimulatory to growth of several murine hybridoma cell lines. None of these researchers combined elevated levels of ethanolamine with elevated levels of glutamine, choline, tryptophan and other amino acids as we have found necessary for optimum product expression. Several other serum-free media do not include ethanolamine (T. Chang, et al., *J. Immunol. Methods,* 1980, 39:369–375) and a review by Iscove (N. N. Iscove, Culture of Lymphocytes and Hemopoietic Cells in Serum-Free Medium p. 169–185 in Methods for Serum-Free Culture of neuronal and Lymphoid Cell Lines, Alan R. Liss Inc., NY 1984) identifies choline and inositol as essential, but does not mention ethanolamine. We have found that ethanolamine is effective when supplemented to a level of approximately 1–10 mg/L, and can be included at up to at least 20 mg/L without apparent toxicity.

It should be understood that choline and ethanolamine can be provided in various forms including phosphocholine and phosphoethanolamine or phosphatidylcholine and phosphatidyletanolamine. The relative effectiveness of these various forms will depend on the ability of the specific cell line to take up (transport) and metabolize the complex forms.

Supplementation of standard media with phospholipid precursors alone is not sufficient to achieve the desired maximum extension of culture longevity and product production. Rather, phospholipid precursors act in synergy with the other components described. The phospholipid precursors may be added to media as a microemulsion using a suitable emulsifier, preferably pluronic polyol F68.

C. Tryptophan

Tryptophan is recognized as an essential amino acid and is included in typical serum-supplemented and serum-free media at 2–20 mg/L, with the exception of Waymouth's MB752/1 medium for L-929 cells where it is present at 40 mg/L. Several researchers have attempted to optimize media by supplementation with increased levels of each amino acid added separately. Typical of these, Barns and Iscove (N. N. Iscove, Culture of Lymphocytes and Hemopoietic Cells in Serum-Free Medium p. 169–185 in Methods for Serum-Free Culture of Neuronal and Lymphoid Cells) have both tested supplementation of media with each of the standard amino acids, and neither found addition of tryptophan at greater than standard levels to be stimulatory. We have found that tryptophan supplementation is essential to achieving the desired increase in culture longevity and product titre. For optimal effect, tryptophan is supplemented to levels higher than those typically taught in the literature, or greater than 20 mg/L, and can be added at up to at least 250 mg/L without toxic effect.

Supplementation of standard media with tryptophan alone is not sufficient to achieve the desired effect. Rather, tryptophan at elevated concentrations acts in synergy with the other components of the Primary Supplement to achieve the desired maximum extension of culture growth and longevity, and product production.

D. Other Amino Acids

The recommended Primary Supplement also includes a formulation of amino acids determined to be desirable for expression of a product from a particular cell line.

Amino acids are the essential building blocks for protein synthesis. Supplementation of medium with the components specified provides the basis for increased culture longevity, and hence, for a significantly increased period for product production. Under these conditions, amino acids required for cell maintenance and product synthesis can become depleted. To maximize final product titre, the levels of these amino acids must be increased so as to not become limiting. Amino acid analysis of spent medium using techniques which are known to the analytical chemist (D. H. Speckman, et al., Automatic Recording Apparatus for Use in the Chromatography of Amino Acids, *Analytical Chemistry,* 1958, 30:1190–1206) can be used as a tool to identify those amino acids which are depleted during culture and require supplementation.

Iscove (N. N. Iscove, Culture of Lymphocytes and hemopoietic Cells in Serum-Free Medium p. 169–185 in Methods for Serum-Free Culture of Neuronal and Lymphoid Cells) and others have tested supplementation of media with each of the standard amino acids. Typical of the literature, Iscove found that addition at greater than standard levels of all amino acids tested, (except cystine), was not stimulatory.

Luan (Y. T. Luan, et al., Strategies to Extend Longevity of Hybridomas in Culture and Promote Yield of Monoclonal Antibodies) describes a fed batch strategy, consisting of adding a supplement containing glutamine, essential amino acids (including tryptophan), vitamins (including choline) and serum at various time points during the culture of a murine hybridoma cell line. The medium to which additions was made consisted of DMEM supplemented with fetal calf serum. This method resulted in an increase in culture longevity and increase in final antibody titre. Similarly, Birch (J. R. Birch, et al., Animal Cell Culture, EPA PCT/GB6/00383, 1986) describes fed-batch culture adding a supplement containing glucose, glutamine essential and non-essential amino acids (including tryptophan) during the culture of another murine hybridoma cell line. The medium to which additions was made was also DMEM supplemented with fetal calf serum.

It is important to note regarding Luan and Birch that neither included ethanolamine in their media which we have found to be a highly favored phospholipid precursors for the optimum cell growth and product production effect. Further, while we have found that our supplement can be used effectively in fed-batch and continuous culture, we have found (unlike Luan and Birch) that inclusion of the supplement at the start of culture is also effective (i.e. in contrast to Luan and Birch, nutrient addition during culture is not obligatory using the supplement of the current invention). Additionally, applicants' supplement can be used advantageously with serum-free and protein-free media. Also differentiating the current work, neither Luan and Birch included a defined reducing agent, such as MTG which we have identified, as discussed below, as a preferred embodiment which can result in a further increase in cell product expression.

III. Class I Reagents

The reagents of the Primary Supplement can be combined with additional reagents to produce media having more favorable cell growth and product expression properties. These, or Class I reagents, include, but are not limited to, reducing agents, trace metal ions and/or vitamins. Components of the Class I reagents can be added individually or in combination with the complete set of reagents of the Primary Supplement. The utility of these additional Class I reagents will vary depending on the cell line and basal medium composition.

A. Reducing Agents

The metabolism of glutathione and related sulfhydryl species has been reviewed by Meister (A. Meister, Selective Modification of Glutathione Metabolism, *Science,* 1983, 220:472–477). Yamane (I. Yamane, et al., Effects of Sulfhydryl Groups and Oxygen Tension on the Cell Proliferating Activity of Bovine Serum Albumin in Culture, *Cell Structure and Function,* 1982, 7:133–143) shows that addition of reducing agents can protect cultures from damage associated with high oxygen tension.

Some serum-supplemented media (such as RPMI 1640) contain added glutathione (GH) at 1–15 mg/L. Other reducing agents are not generally included in serum-supplemented media. For example, β-mercaptoethanol (B-ME) and monothioglycerol (MTG) are not typically included in cell culture media, and are not included in any of the media tabulated by Freshey above. In contrast, glutathione or dithiothreitol (DTT) is included in MCDB 110 serum-free medium, but are absent from several other serum-free formulations (CDB 170, MCDB 153, WAJC, HITES, etc.). Iscove's serum-free medium does not contain GH or DTT.

It is important to note that although there are reports of media containing reducing agents, that none of these media contain all of the reagents of the Primary Supplement. For instance, Iscove (N. N. Iscove, Culture of Lymphocytes and Hemopoietic Cells in Serum-Free Medium, p 169–185, in Methods for Serum-Free Culture of Neuronal and Lymphoid Cells) recommends supplementation of his IMDM medium with either B-ME ($5 \times 10^{-5}$ M) or MTG $7.5 \times 10^{-5}$ M. Iscove's medium does not, however, contain ethanolamine or the elevated levels of glutamine, tryptophan and other amino acids required for the synergistic effect observed for cell growth and product expression attributed to reagents of the Primary Supplement. Further, Kawamoto (T. Kawamoto, *Anal. Biochem.,* 1983, 130:445–453) has supplemented a basal medium with several components including ethanolamine (10 M) and B-ME (10 M). Kawamoto's media do not, however, contain the elevated levels of glutamine, tryptophan and other amino acids required for the synergistic effect. Likewise, Kovar (J. Kovar, et al., *Immunol. Letters,* 1984, 7:339–345) developed a serum-free medium containing ethanolamine (20 M), but this medium again contains low levels of glutamine, tryptophan and other amino acids and does not result in the synergy which we have discovered. Kovar (J. Kovar, et al., Serum-Free Medium for Hybridoma and Parental Myeloma Cell Cultivation: A Novel Composition of Growth Supporting Substances) tested β-mercaptoethanol as a possible component in their ethanolamine supplemented RPMI-1640 based serum-free medium. This medium did not contain elevated levels of glutamine, tryptophan, other amino acids, or choline, which we have found favors the optimum synergistic effect. In the absence of these components, Kovar and Frank found B-ME not to be useful and deleted it from their final formulation.

We have found that supplementation of culture media with a reducing agent/sulfhydryl compound can result in an increase in culture longevity and product titre. However, such supplementation is maximally effective when in combination with the complete Primary Supplement. Reducing agent/sulfhydryl compounds for use include β-mercaptoethanol, monothioglycerol (MTG), dithiothreitol, glutathione, thioglycolate, and cystine. More preferred are thiol molecules which have hydroxyl group(s) such as (β-mercaptoethanol) B-ME, (monothioglycerol) MTG and (dithiothreitol) DTT. Most preferred are monothiol compounds of this class such as B-ME and MTG. These are effective at concentrations above 0.1 mg/L and are not toxic at up to at least 10 mg/L. A preferred concentration is 0.5–100 mg/L for either B-ME or MTG. More preferred is 10 mg/l for MTG.

B. Metal Ions

Metal ions are essential for animal cell culture and are included in typical media as components of salt and trace element mixtures, or as components of undefined supplements such as serum (K. Higuchi, Cultivation of Animal Cells in Chemically Defined Media—A Review p. 111–136). In media supplemented with the reagents of the Primary Supplement, high cell densities can be reached such that availability of certain metal ions, if included only at the levels incorporated in standard media designed to support lower cell densities, can become limiting. Therefore, in a preferred embodiment of the current invention, metal ions are also included in the supplement as found to be necessary for a particular cell line. At the high concentrations that can be required, solubility limits of some metal ions may limit the maximum concentration that can be added with beneficial effect. Therefore, a further preferred embodiment is to supply necessary metal ions along with a suitable chelating agent. The chelating agent must be non-toxic at the concentrations added, and must bind the required metal ions in a reversible manner such that they may be held in solution at adequate concentration, but will be delivered to the cells in an active form.

Analysis of the spent medium using techniques which are well known to the analytical chemist ("Flame Photometry", Chpt. 11, in H. Willard, et al., Instrumental Methods of Analysis, Van Nostrand Co., 1965) can be used as a tool to identify those metal ions which are utilized and may require supplementation. Some metal ions which may require supplementation include, but are not limited to, calcium, magnesium, molybdenum, cobalt, copper, manganese, zinc, selenium and iron. A more extensive list is given by Hamilton and Ham (W. Hamilton, et al., Clonal Growth of Chinese Hamster Cell Lines in Protein-Free Media, *In Vitro,* 1977, 13(9):537–547).

Various metal chelators have been used in cell culture. Natural proteins which can serve this function include transferrin and ferritin, especially to chelate iron, and albumin to chelate a variety of multivalent metal ions. Some other chelators which have been used especially to chelate iron include pyridoxyl isonicotinoyl hydrazone, choline citrate, citrate (C. III, T. Brehm, et al., Species Specificity of Iron Delivery in Hybridomas, *In Vitro Cell. Develop. Biol.,* 1988, 24(5):38) and acetylacetonate (L. Rasmussen, et al., Utilization of Iron Complexes in an Animal Cell, *J. Cellular Physiol.,* 1985, 122:155–158). We have found citrate at about 0.1–10 mM to be an effective chelator capable of supplying several multivalent metal ions. In addition, a variety of other organic acids such as malic acid, succinic acid, fumaric acid and alpha ketoglutaric acid are effective chelators. Citrate is the preferred chelator because of its capacity to chelate iron. Indeed, in those media that are devoid of insulin and transferrin, high levels of iron are used, typically supplied to the cells as $FeCl_3.6H_2O$ or $FeSO_4$, with high levels of citrate. For example, in Example 8, $FeCl_3$ is 27 mg/l and Na citrate at 294 mg/l.

C. Vitamins

Vitamins are essential for animal cells in culture and are generally included in cell culture media (K. Higuchi, Cultivation of Animal Cells in Chemically Defined Media—A Review p. 111–136 in *Advan. Appl. Microbiol.,* 1973, 16:111). In media supplemented only with the Primary Supplement composition, high cell densities can be reached such that availability of certain vitamins, if included only at the levels incorporated in standard media designed to support lower cell densities, can become limiting. Therefore, in a further preferred embodiment of the current invention, vitamins may also be included in the supplement as found to be necessary for a particular cell line. Vitamins which may become limiting include, but are not limited to, p-aminobenzoic acid, biotin, folic acid, folinic acid, nicotinamide, pantothenate, pyridoxine, riboflavin, flavin adenine dinucleotide, ascorbic acid, thiamine and vitamin B-12.

Having generally described the media supplements of the instant invention, several limitations associated with their use, as well as ways to circumvent the limitations warrant discussion.

Firstly, although it is convenient to define classes of reagents that can be readily combined with culture media that is fed to cells without later during the culture period having to refeed the cells, it will be appreciated by those skilled in the art that similar favorable effects can be gained by adding individual reagents to the culture media during the culture period, so as to maintain their concentrations at the levels provided by the supplements. This is most apparent with regard to glutamine, which can be added in combination with the other reagents of the Primary Supplement, or omitted and individually added and maintained at the desired level.

Secondly, the concentrations of reagents that are used in the various supplements will vary over the ranges stated, and are a function of both the cell culture media to which the supplements are added, as well as the particular cell type cultured. The optimal concentrations of the reagents are readily determined by those skilled in the art.

Thirdly, with the exception of reagents of the Primary Supplement, all of which must be present in the supplements for maximum cell culture benefit, only one of the Class I reagents need be present for maximum advantageous results.

Fourthly, it will be realized that for optimal results, the basal medium to which the supplement is added must be appropriate for the cell line of interest, with key nutrients available at adequate levels to enhance cell growth or product expression. Thus, for example, it may be necessary to increase the level of glucose (or other energy source) in the basal medium, or to add glucose (or other energy source) during the course of culture, if this essential energy source is found to be depleted and to thus limit cell growth or product expression.

The following examples illustrate the invention, but are not intended to limit it in any manner. For instance, hybridomas and antibodies are illustrative of cell lines that can be successfully grown and harvested, respectively in media supplemented with the instant compositions. However, such media are not limited to growing hybridomas or harvesting antibody, but rather can be used to grow a wide variety of cells that produce a broad range of products. It will further be appreciated by those skilled in the art that various components used to formulate the media presented herein can be substituted by chemically related compounds without adversely affecting the formulations.

EXAMPLE 1

A Representative Commercial Medium Formulation

Ventrex HL-1 is a medium, representative of state-of-the-art commercially available media for cell culture. Product literature indicates that this medium "was designed for use in the culture of hybridomas and lymphoid cells". The medium is claimed to be effective for growth of many transformed and established cell lines, and especially for production of monoclonal antibodies from murine and human hybridomas. A list of 55 cell lines grown successfully in this medium is presented in *Current Concepts,* 1(1):5, published by Ventrex, 217 Read St., Portland, Ma.

FIG. 1 shows the growth and product expression from a hybridoma cell line, D-234, producing a human monoclonal antibody in HL-1 medium. The maximum viable cell density of $1.3 \times 10^6$ cell/ml is reached at 120 hours and the culture dies rapidly thereafter. The maximum total cell density is $2 \times 10^6$ cells/ml. The final antibody titre is 70 mg/L.

The hybridoma D-234 is on deposit with the American Type Culture Collection with Accession No. HB 8598.

The hybridoma produces an IgM antibody which was assayed using standard ELISA Techniques.

EXAMPLE 2

Serum-Free Hybridoma Medium Formulation

Table I, column 1, shows a typical serum-free medium formulation (50% RPMI, 50% DME, bovine insulin (5 mg/L), human transferrin (5 mg/L), selenium (5 g/L), 0.1% Pluronic polyol (F68). This medium is similar to several compositions reported in the literature.

Figure 2:
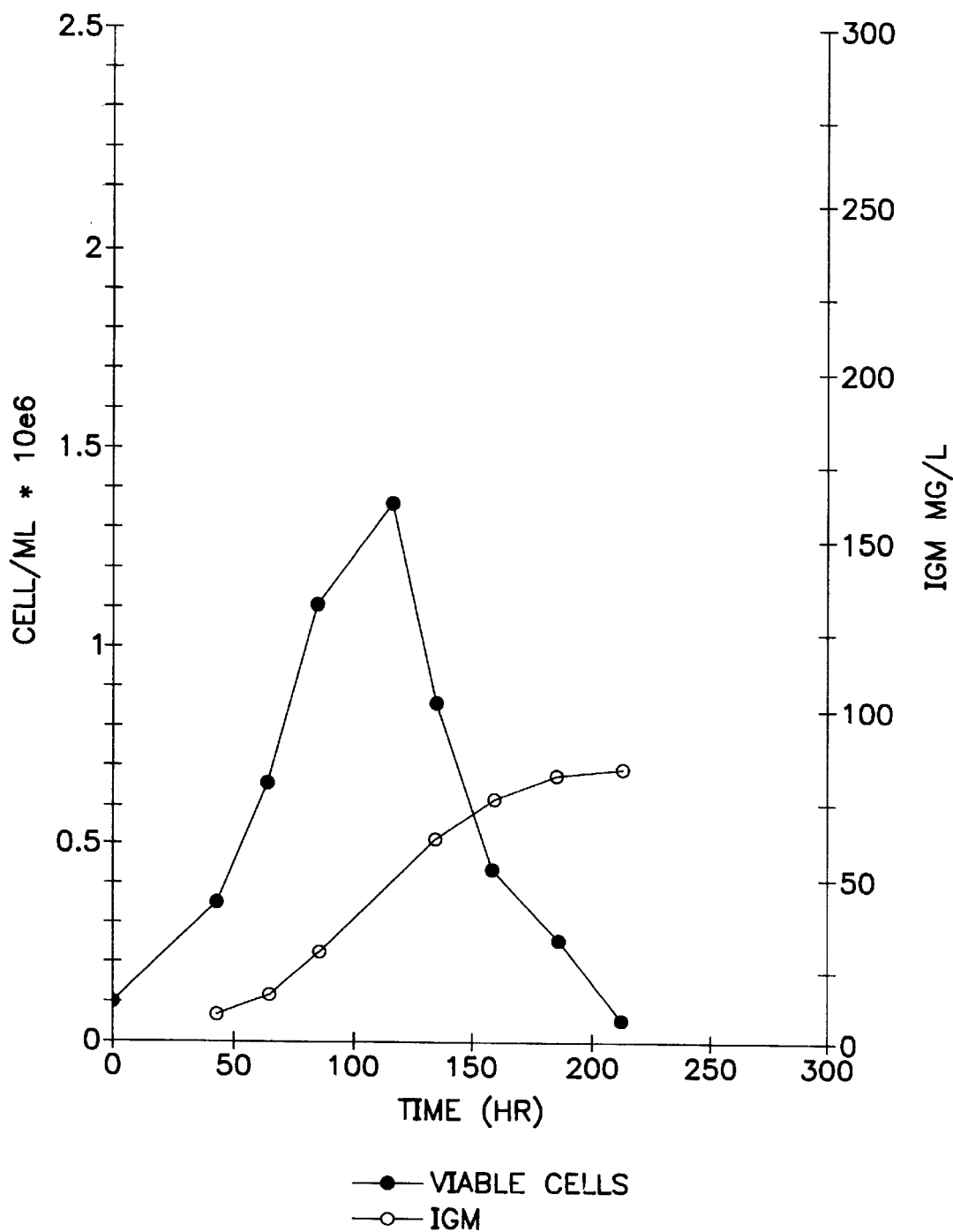
FIG. 2 shows the growth properties and levels of antibody produced by D234 in a standard serum free medium composition representative of compositions described in the cell culture literature.

FIG. 2 shows growth and product expression by the D234 hybridoma in the medium of Table I, column 1. Growth and product expression are similar to that in the commercially available HL-1 medium. The maximum viable cell density is $1.3 \times 10^6$ cells/ml. The final antibody titre is 80 mg/L.

TABLE I

| | (mg/l) | | | | | | |
|---|---|---|---|---|---|---|---|
| | 1 | 2 | 3 | 4 | 5 | 6 (DM30) | 7 (DM40) |
| 1. $CaCl_2$ | 0.0000 | 0.0000 | 400.0000 | 100.0000 | 200.00000 | 0 | 0 |
| 2. $Ca(NO_3)_2 \cdot 4H_2O$ | 50.0000 | 50.0000 | 40.0000 | 50.0000 | 45.00000 | 50 | 50 |
| 3. $Fe(NO_3)_3 \cdot 9H_2O$ | 0.0500 | 0.0500 | 0.0400 | 0.0500 | 0.04500 | 0 | 0 |
| 4. KCl | 400.0000 | 400.0000 | 560.0000 | 400.0000 | 480.00000 | 400 | 400 |
| 5. $MgSO_4$ | 73.5000 | 73.5000 | 242.8000 | 173.5000 | 158.15000 | 150 | 150 |
| 6. NaCl | 6000.0000 | 6000.0000 | 5300.0000 | 6000.0000 | 5650.00000 | 3800 | 3800 |
| 7. $NaH_2PO_4 \cdot H_2O$ | 625.0000 | 625.0000 | 732.0000 | 625.0000 | 678.50000 | 830 | 830 |
| 8. $Na_2HPO_4$ | 400.5000 | 400.5000 | 320.4000 | 400.5000 | 360.45000 | 360 | 360 |
| 9. | | | | | | | |
| 10. Glucose | 2800.0000 | 3800.0000 | 2700.0000 | 4800.0000 | 2700.00000 | 1000 | 1000 |
| 11. Glutathione | 0.5000 | 0.5000 | 0.4000 | 0.5000 | 0.45000 | 0.5000 | 0.5000 |
| 12. HEPES | 2979.0000 | 2979.0000 | 2383.2000 | 2979.0000 | 2681.10000 | 2979 | 2979 |
| 13. Na Pyruvate | 55.0000 | 55.0000 | 44.0000 | 1155.0000 | 49.50000 | 110 | 110 |
| 14. $NaHCO_3$ | 2850.0000 | 2850.0000 | 2350.0000 | 2850.0000 | 2600.00000 | 2850 | 2850 |
| 15. Phenol Red | 10.0000 | 10.0000 | 8.0000 | 10.0000 | 9.00000 | 10.0000 | 10.0000 |
| 16. pAmino Benzoic Acid | 0.5000 | 0.5000 | 0.4640 | 1.0000 | 0.48200 | .5000 | .5000 |
| 17. Biotin | 0.1000 | 0.1000 | 0.1120 | .2000 | 0.10600 | .1000 | .1000 |
| 18. Ca Pantothenate | 2.1250 | 2.1250 | 1.7016 | 4.0000 | 1.91330 | 2.0000 | 2.0000 |
| 19. Folic Acid | 2.5000 | 2.5000 | 1.6000 | 4.0000 | 1.80000 | 2.5 | 2.5 |
| 20. Nicotinamide | 2.5000 | 2.5000 | 2.0000 | 5.0000 | 2.25000 | 2.5 | 7.5 |
| 21. Pyridoxal HCl | 2.0000 | 2.0000 | 1.6000 | 4.0000 | 1.80000 | 0 | 0 |
| 22. Pyridoxine HCl | 0.5000 | 0.5000 | 0.4800 | 1.0000 | 0.49000 | 2.0 | 2.0 |
| 23. Riboflavin | 0.3000 | 0.3000 | 0.2560 | .6000 | 0.27800 | 0.3 | 0.3 |
| 24. Thiamine HCl | 2.5000 | 2.5000 | 2.0160 | 5.0000 | 2.25800 | 2.5 | 2.5 |
| 25. Vitamin B12 | 0.0025 | 0.0025 | 0.0500 | .2400 | 0.02625 | .0025 | .0025 |
| 26. Choline Chloride | 3.5000 | 23.5000 | 22.8000 | 23.5000 | 23.15000 | 75 | 75 |
| 27. Inositol | 21.0000 | 41.0000 | 24.8800 | 41.0000 | 27.94000 | 50 | 50 |
| 28. Ethanolamine | 0.0000 | 10.0000 | 0.8 | 10.0000 | 0.9 | 20 | 20 |
| 29. Glycerol | 0.0000 | 200.0000 | 0.0000 | 200.0000 | 180.00000 | 0 | 0 |
| 30. Glutamine | 1160.0000 | 1160.0000 | 1160.0000 | 1160.0000 | 1180.00000 | 8–40mM | 8–40mM |
| 31. Pluronic Polyol F68 | 1000.0000 | 1000.0000 | 1000.0000 | 1000.0000 | 1000.00000 | 1000 | 1000 |
| 32. Insulin | 5.0000 | 5.0000 | 4.0000 | 5.0000 | 4.50000 | 0 | 0 |
| 33. Transferrin | 5.0000 | 5.0000 | 4.0000 | 5.0000 | 4.50000 | 0 | 0 |
| 34. $H_2SeO_3$ | 0.005 | 0.0050 | 0.0040 | 0.0050 | 0.00450 | 0 | 0 |
| 35. $Na_2SeO_3$ | | | | | | 0.08 | 0.08 |
| 36. $FeCl_3 \cdot 6H_2O$ | 0.0000 | 0 | 0.0000 | 1.6000 | 0 | 29.7 | 29.7 |
| 37. $(NH_4)_6Mo_7O_{24} \cdot 4H_2O$ | 0.0000 | 0 | 0.0080 | 0.1000 | 0.00400 | .4000 | .4000 |
| 38. $CoCl_2 \cdot 6H_2O$ | 0.0000 | 0.1000 | 0.0100 | 0.1000 | 0.00500 | .4000 | .4000 |
| 39. $CuCl_2 \cdot 2H_2O$ | 0.0000 | 0 | 0.0400 | 0.1000 | 0.02000 | .4000 | .4000 |
| 40. $MnCl_2 \cdot 4H_2O$ | 0.0000 | 0.1000 | 0.0040 | 0.1000 | 0.00200 | .4000 | .4000 |
| 41. $ZnCl_2$ | 0.0000 | 0 | 0.0080 | 0.1000 | 0.00400 | .4000 | .4000 |
| 42. $FeSO_4 \cdot 7H_2O$ | 0.0000 | 0.0000 | 0.1100 | 0.0000 | 0.05500 | 0 | 0 |

TABLE I-continued

| | (mg/l) | | | | | | |
|---|---|---|---|---|---|---|---|
| | 1 | 2 | 3 | 4 | 5 | 6 (DM30) | 7 (DM40) |
| 43. Niacin | 0.0000 | 0 | 0.0320 | 0.0000 | 0.01600 | 0 | 0 |
| 44. Hydroxyproline | 0.0000 | 0 | 160.0000 | 0.0000 | 80.00000 | 0 | 0 |
| 45. Beta Alanine | 0.0000 | 0 | 60.0000 | 0.0000 | 30.00000 | 0 | 0 |
| 46. Malic Acid | 0.0000 | 0 | 10.7200 | 0.0000 | 5.36000 | 0 | 0 |
| 47. α Ketoglutaric Acid | 0.0000 | 0 | 5.9200 | 0.0000 | 2.96000 | 0 | 0 |
| 48. Succinic Acid | 0.0000 | 0 | 0.9600 | 0.0000 | 0.48000 | 0 | 0 |
| 49. Fumaric Acid | 0.0000 | 0 | 0.8800 | 0.0000 | 0.44000 | 0 | 0 |
| 50. D Serine | 0.0000 | 0 | 40.0000 | 0.0000 | 20.00000 | 0 | 0 |
| 51. Sucrose | 0.0000 | 0 | 330.0000 | 0.0000 | 165.00000 | 0 | 0 |
| 52. Maltose | 0.0000 | 0 | 200.0000 | 0.0000 | 100.00000 | 0 | 0 |
| 53. Ethanol | 0.0000 | 0.0000 | 640.0000 | 0 | 720.00000 | 0 | 0 |
| 54. Tween 80 | 0.0000 | 0.0000 | 1.6000 | 0 | 1.80000 | 0 | 0 |
| 55. Lecithin | 0.0000 | 0.0000 | 0.8000 | 0 | 0.90000 | 0 | 0 |
| 56. Linoleic Acid | 0.0000 | 0.0000 | 0.8000 | 0 | 0.90000 | 0 | 0 |
| 57. Cholesterol | 0.0000 | 0.0000 | 0.4000 | 0 | 0.45000 | 0 | 0 |
| 58. α Tocopherol Acetate | 0.0000 | 0.0000 | 0.4000 | 0 | 0.45000 | 0 | 0 |
| 59. Monothioglycerol | 0.0000 | 0.0000 | 0.8000 | 10.0000 | 0.90000 | 10 | 10 |
| 60. Citrate | 0 | 0 | 0 | 258.0000 | 0 | 294.0 | 294.0 |
| 1. ARG | 142 | 542 | 246.2 | 794 | 194.1 | 750 | 750 |
| 2. ASP | 25 | 125 | 280.0 | 125 | 152.5 | 700 | 1400 |
| 3. ASP AC. | 10 | 50 | 274.0 | 50 | 142.0 | 0 | 0 |
| 4. CYSTINE | 49 | 49 | 59.2 | 195 | 54.1 | 0 | 0 |
| 5. GLUT.AC. | 10 | 50 | 308.0 | 50 | 159.0 | 50 | 50 |
| 6. GLY | 20 | 40 | 56.0 | 40 | 38. | 250 | 250 |
| 7. HIS | 28 | 58 | 62.4 | 120 | 45.2 | 300 | 300 |
| 8. ISOLEU | 78 | 178 | 212.4 | 282 | 145.2 | 1000 | 1000 |
| 9. LEU | 78 | 178 | 112.4 | 282 | 95.2 | 1200 | 1200 |
| 10. LYS. HCL | 93 | 173 | 214.4 | 317 | 153.7 | 1000 | 1000 |
| 11. MET | 22 | 52 | 217.6 | 82 | 119.8 | 400 | 400 |
| 12. PHENYLALA | 40 | 70 | 232.0 | 136 | 136.0 | 400 | 400 |
| 13. PRO | 10 | 50 | 108.0 | 50 | 59.0 | 50 | 50 |
| 14. SER | 36 | 136 | 68.8 | 96 | 52.4 | 400 | 400 |
| 15. THREO | 58 | 98 | 86.4 | 194 | 72.2 | 500 | 500 |
| 16. TRP | 10 | 120 | 28.0 | 140 | 19.0 | 250 | 250 |
| 17. TYRO | 46 | 146 | 86.8 | 158 | 66.4 | 500 | 500 |
| 18. VAL | 57 | 97 | 145.6 | 191 | 101.3 | 600 | 600 |

EXAMPLE 3

Medium Containing Primary Supplement—Addition Of Glutamine Before And During The Culture Period Table I, column 4, shows a composition wherein the standard medium has been supplemented with the reagents of the Primary Supplement (glutamine at 8 mM, tryptophan at 140 mg/L, choline at 20 mg/L, ethanolamine at 10 mg/L and other amino acids increased in concentration by typically around 3 fold the concentration in the basal medium). In initial studies it was determined that the glucose level in the basal medium could be depleted and limit culture growth and longevity. Therefore, in addition to being included in the basal medium, additional glucose was added during the course of the culture period. Further, glutamine, in addition to being incorporated in the Primary Supplement to the medium at the start of culture, was also added at day 4, 8 and 12 such that the total glutamine supplied was equivalent to 20 mMoles per liter of culture.

Figure 3:
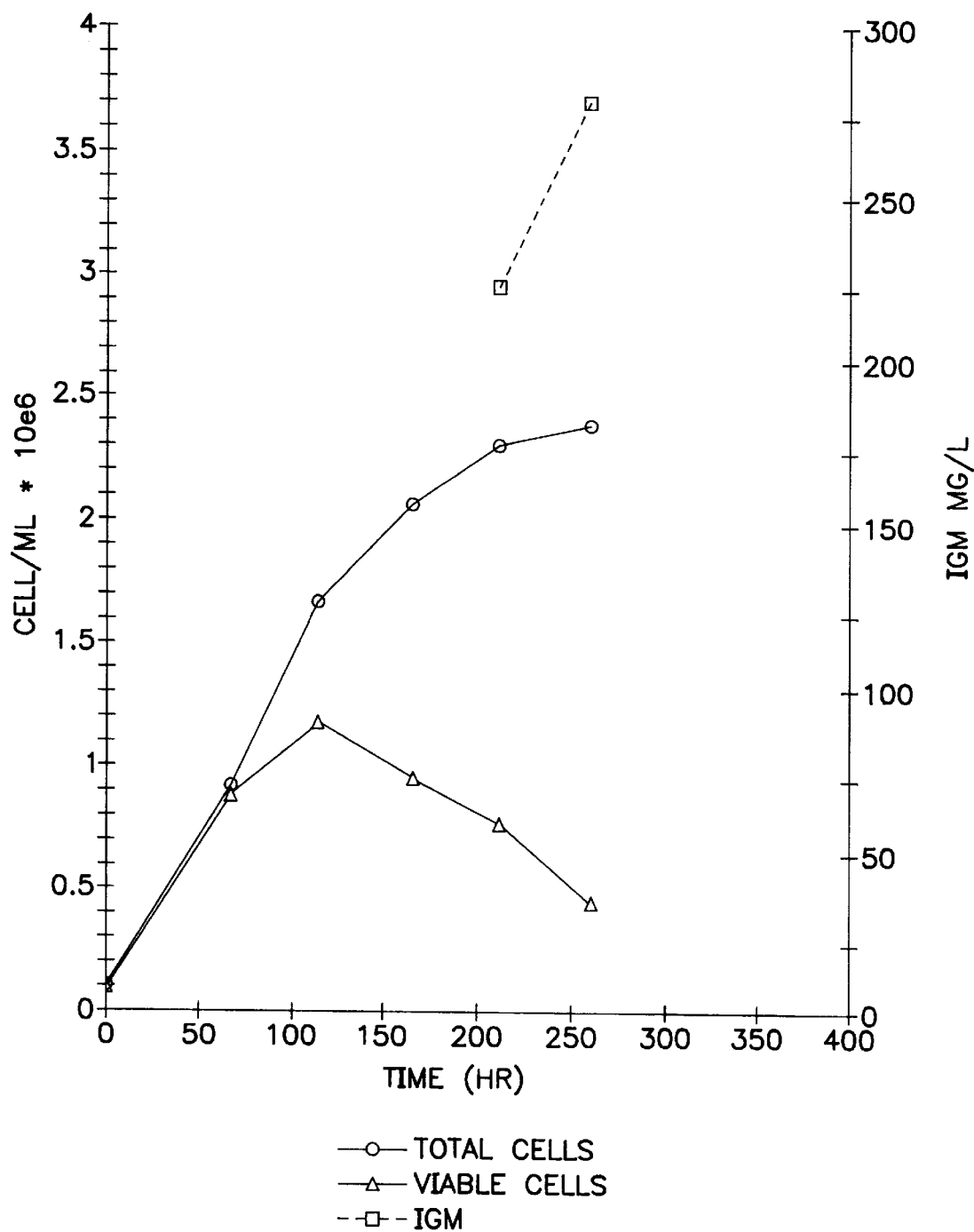
FIG. 3 shows the growth properties and levels of antibody produced by D234 in media supplemented with reagents of the Primary Supplement.

FIG. 3 shows growth and product expression by D234 in the supplemented medium. Maximum viable cell density of $1.2 \times 10^6$ cell/ml is reached at 120 hours, thereafter the culture is maintained in a pseudo-stationary phase, where cell growth approximately balances cell death such that the viable cell concentration declines only slowly over a period for 100 hours. The total cell density continues to rise to $2.5 \times 10^6$ cells/ml. Cells continue to express product over the pseudo-stationary phase, and a final titre of 290 mg human antibody per liter is reached.

EXAMPLE 4

Medium Containing Primary Supplement—Addition Of Glutamine At The Start Of The Culture Period Only D234 was grown in medium and conditions similar to those in Example 3, except that glutamine was included in the Primary Supplement to make the concentration of glutamine 20 mM at the start of culture, and glutamine was not added thereafter. Growth and product expression were equivalent to those in Example 3.

EXAMPLE 5

Medium Containing Primary Supplement and Class I Reagent

Table I, column 2, shows a composition wherein standard medium has been supplemented with the reagents of the Primary Supplement as well as with mono-thioglycerol (a Class I reagent) at 10 mg/L. Glucose and glutamine were supplied as in Example 3.

Figure 4:
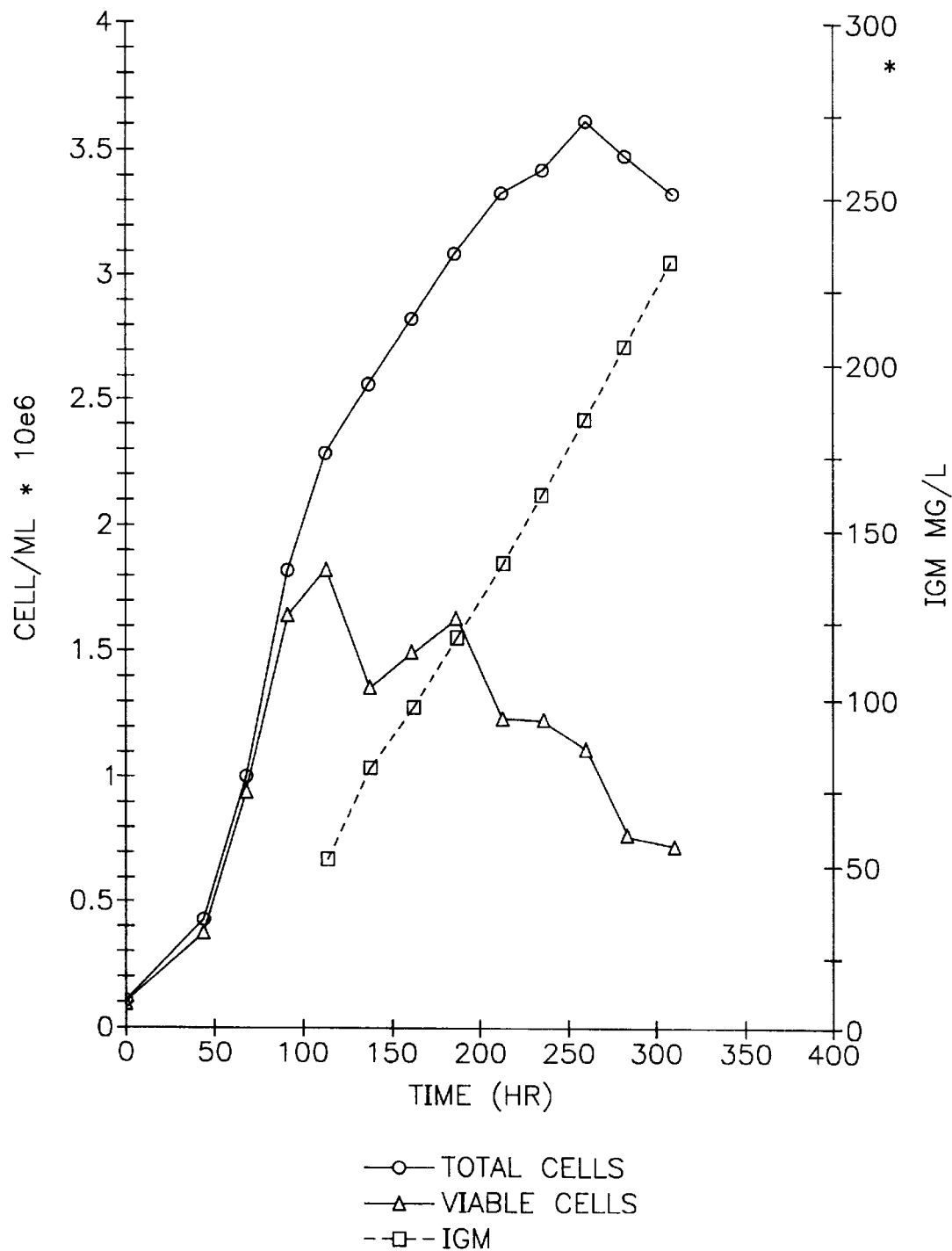
FIG. 4 shows the growth properties and levels of antibody produced by D234 in media supplemented with reagents of the Primary Supplement and a Class I reagent.

FIG. 4 shows growth and product expression by D234 in the supplemented medium. Maximum viable cell density of $1.9 \times 10^6$ cell/ml is reached at 120 hours. Thereafter, the culture is maintained in a pseudo-stationary phase, where cell growth rate approximately balances the rate of cell death such that the viable cell concentration declines only slowly over a period of 150 additional hours. Total cell density continues to climb to $3.8 \times 10^6$ cells/ml. Cells continue to express product over the pseudo-stationary phase period and a final titre of 230 mg human antibody per L is reached.

EXAMPLE 6

Supplement Used In Combination With Lipid Emulsion

Table I, column 3, shows a composition in which the typical cell culture medium has been supplemented with the reagents of the Primary Supplement (8 mM glutamine, 28 mg/L tryptophan, 22.8 mg/L choline, 0.8 mg/L ethanolamine, and other amino acids supplemented to typically around 3 fold the basal medium concentration), and with Class I reagents (1 mg/L monothioglycerol, vitamin B-12 and trace elements including manganese and molybdenum, cobalt, copper, zinc and iron). Additionally, the medium contains lipids (linoleic acid, tween 80, lecithin, cholesterol and vitamin E). Additionally, glucose and glutamine was added during the culture period as described in Example 3.

Figure 5:
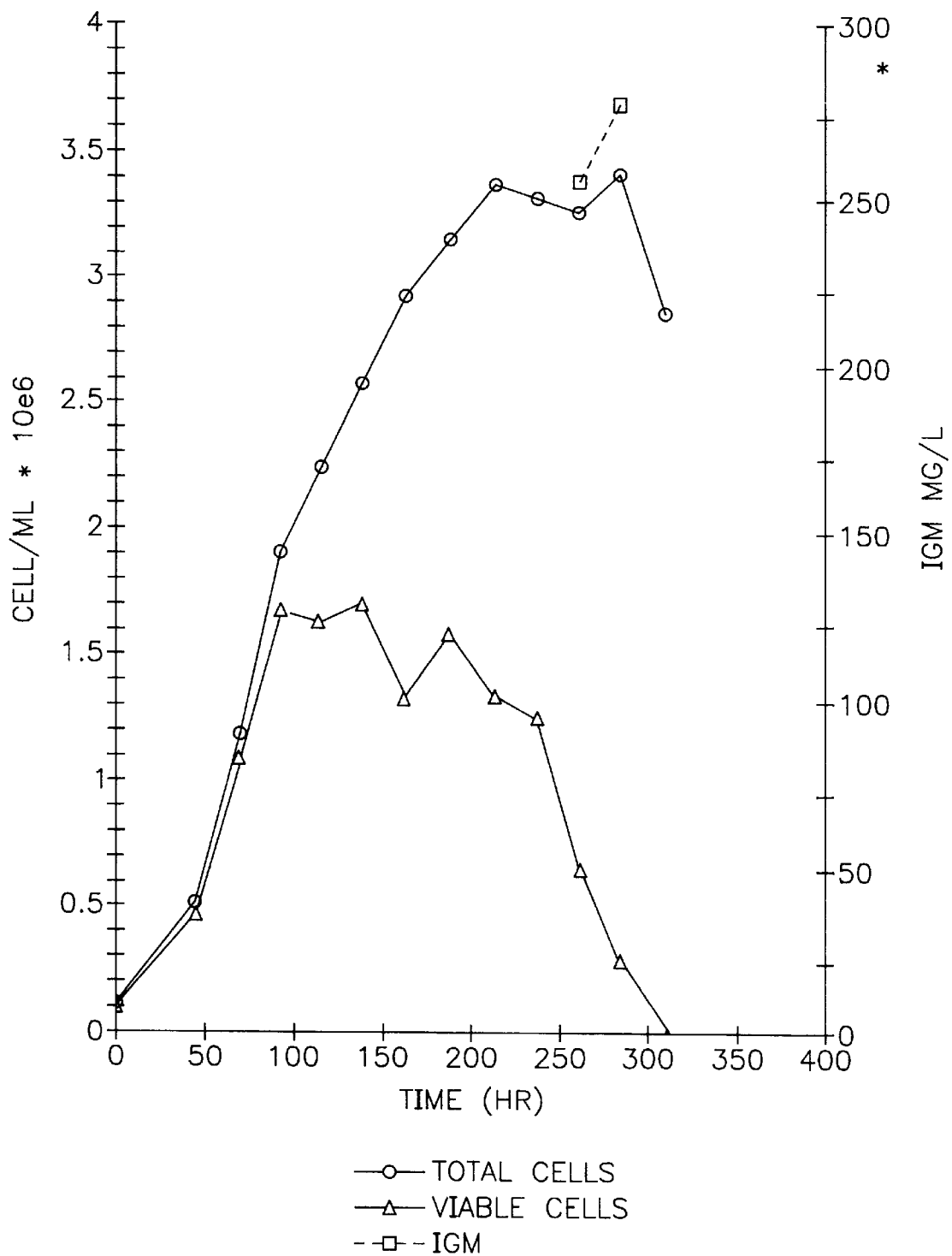
FIG. 5 shows the growth properties and levels of antibody produced by D234 in media supplemented with reagents of the Primary and Class I Supplement and used in combination with lipid supplementation.

FIG. 5 shows the growth and product expression by D234 in the supplemented medium. Maximum viable cell density of $1.7 \times 10^6$ cells/ml is reached at 80 hours. Thereafter, the culture is maintained in a pseudo-stationary phase during which growth continues at approximately 50% of the maximum exponential phase growth rate which approximately balances the rate of death such that the viable cell concentration declines only slowly over a period of 150 additional hours. Total cell density continues to climb to $3.5 \times 10^6$ cells/ml. Cells continue to express product over the pseudo-stationary phase period and a final titre of 275 mg human antibody per L is reached.

EXAMPLE 7

Use Of Supplement In Fed-Batch Culture

The supplement of the present invention can be used beneficially in fed-batch, as well as in simple batch culture. Table I, column 5, shows the standard medium supplemented with reagents of the Primary Supplement and Class I reagents, as well as with lipids. This medium is similar to that of Example 6 (Table I, column 3).

This medium was used for growth of D234 in a fed-batch process. After 120 hours, additional supplement was added as shown in Table II. After 220 hours, glutamine was further supplemented with another 5 mmoles/L of culture.

Figure 6:
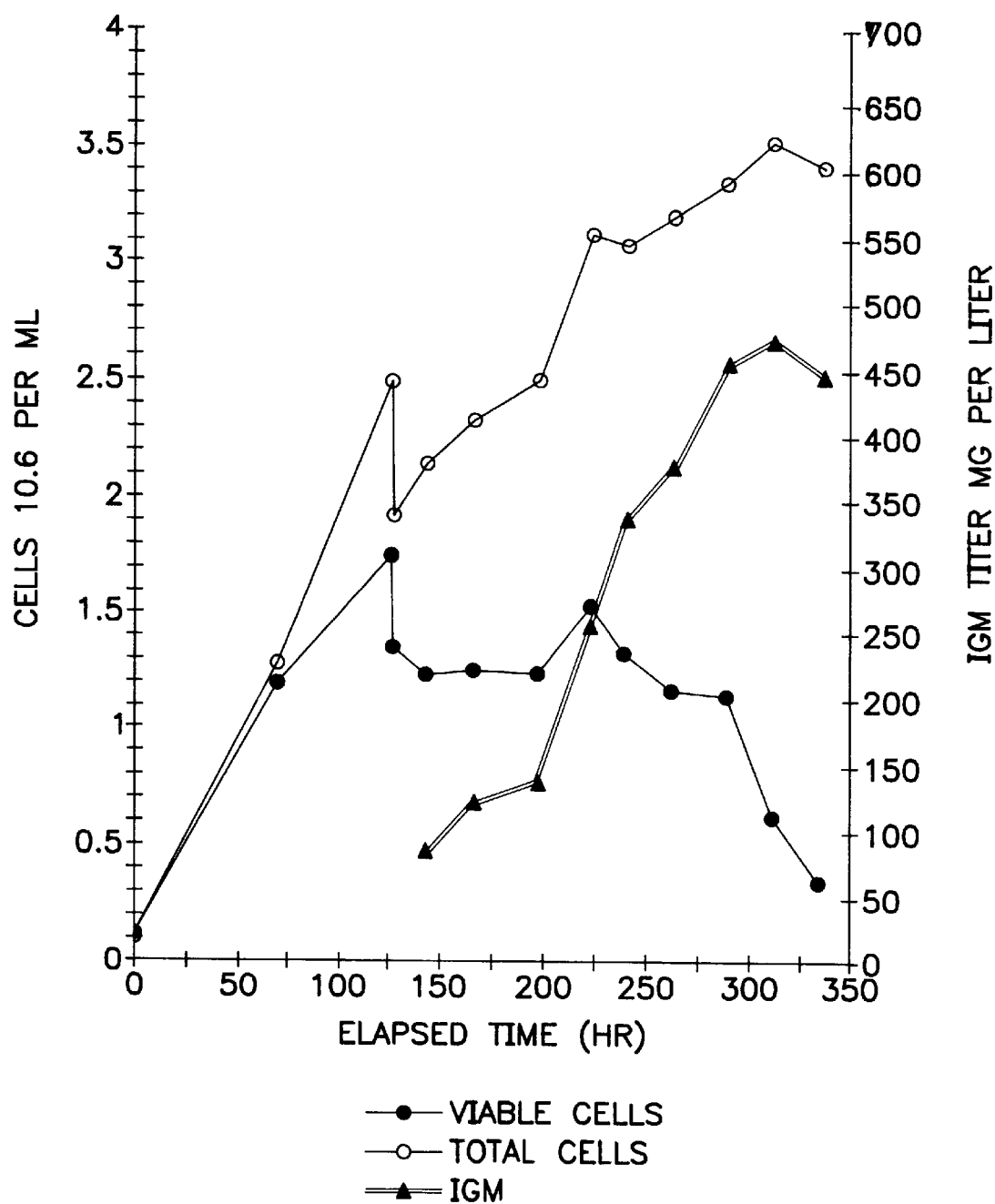
FIG. 6 shows the hybridoma D234 grown in Fed-batch with media supplemented with reagents of the Primary and Class I Supplements and lipids.

FIG. 6 shows the growth and product expression by D234 in the supplemented fed-batch culture. Maximum viable cell density of $1.8 \times 10^6$ cells/ml is reached at 130 hours. Thereafter, the culture is maintained in a pseudo-stationary phase during which growth continues at approximately 20% of the maximum exponential phase growth rate which approximately balances the rate of death such that the viable cell concentration declines only slowly over a period of 190 additional hours. Total cell density continues to climb to $3.7 \times 10^6$ cells/ml. Cells continue to express product over the pseudo-stationary phase period and a final titre of 470 mg human antibody per L is reached.

Other feeding strategies have also been tested wherein the nutrients are added to a similar total final concentration as in the above sample, but are added at different schedules. Subdivision of the supplement addition into nearly equal daily additions beginning after 190 hours gives results similar to those described above. Slow continuous feeding also gives similar results.

TABLE II

| | |
|---|---|
| 1. $CaCl_2$ | 400.0000 |
| 2. $Ca(No_3)_2 \cdot 4H_2O$ | 0.0000 |
| 3. $Fe(NO_3)_3 \cdot 9H_2O$ | 0.0000 |
| 4. KCl | 240.0000 |
| 5. $MgSO_4$ | 184.0000 |
| 6. NaCl | 500.0000 |
| 7. $NaH_2PO_4 \cdot H_2O$ | 232.0000 |
| 8. $Na_2HPO_4$ | 0.0000 |
| 9. Glucose | 500.0000 |
| 10. Glutathione | 0.0000 |
| 11. HEPES | 0.0000 |
| 12. Na Pyruvate | 0.0000 |
| 13. $NaHCO_3$ | 0.0000 |
| 14. Phenol Red | 0.0000 |
| 15. pAmino Benzoic Acid | 0.0640 |
| 16. Biotin | 0.3200 |
| 17. Ca Pantothenate | 0.0016 |
| 18. Folic acid | 0.0160 |
| 19. Nicotinamide | 0.0000 |
| 20. Pyridoxal HCl | 0.0000 |
| 21. Pyridoxine HCl | 0.0800 |
| 22. Riboflavin | 0.0160 |
| 23. Thiamine HCl | 0.0160 |
| 24. Vitamin B12 | 0.0480 |
| 25. Choline Chloride | 4.0000 |
| 26. Inositol | 0.0800 |
| 27. Ethanolamine | 0.0000 |
| 28. Glycerol | 0.0000 |
| 29. Glutamine | 1660.0000 |
| 30. Pluronic Polyol F68 | 200.0000 |
| 31. Insulin | 0.0000 |
| 32. Transferrin | 0.0000 |
| 33. $Na_2SeO_3$ | 0.0000 |
| 34. $FeCl_3$ | 0.0000 |
| 35. $(NH_4)_6Mo_7O_{24} \cdot 4H_2O$ | 0.0080 |
| 36. $CoCl_2 \cdot 6H_2O$ | 0.0100 |
| 37. $CuCl_2 \cdot 2H_2O$ | 0.0400 |
| 38. $MnCl_2 \cdot 4H_2O$ | 0.0040 |
| 39. $ZCl_2$ | 0.0080 |
| 40. $FeSO_4 \cdot 7H_2O$ | 0.1100 |
| 41. Niacin | 0.0320 |
| 42. Hydroxyproline | 160.0000 |
| 43. Beta Alanine | 60.0000 |
| 44. Malic acid | 10.7200 |
| 45. alpha Ketoglutaric acid | 5.9200 |
| 46. Succinic acid | 0.9600 |
| 47. Fumaric acid | 0.8800 |
| 48. D Serine | 40.0000 |
| 49. Sucrose | 330.0000 |
| 50. Maltose | 200.0000 |
| 51. Ethanol | 0.0000 |
| 52. Tween 80 | 0.0000 |
| 53. Lecithin | 0.0000 |
| 54. Linoleic acid | 0.0000 |
| 55. Cholesterol | 0.0000 |
| 56. alpha Tocopherol acetate | 0.0000 |
| 57. Monothioglycerol | 20.0000 |
| 58. Glucose | 500.0000 |
| 1. ARG | 132.6 |
| 2. ASP | 260.0 |
| 3. ASP AC. | 266.0 |
| 4. CYSTINE | 20.0 |
| 5. GLUT.AC. | 300.0 |
| 6. GLY | 40. |
| 7. HIS | 40.0 |
| 8. ISOLEU | 150.0 |
| 9. LEU | 50.0 |
| 10. LYS. HCL | 140.0 |
| 11. MET | 200.0 |
| 12. PHENYLALA | 200.0 |

TABLE II-continued

| | | |
|---|---|---|
| 13. PRO | | 100.0 |
| 14. SER | | 40.0 |
| 15. THREO | | 40.0 |
| 16. TRP | | 20.0 |
| 17. TYRO | | 50.0 |
| 18. VAL | | 100.0 |

Finally, Table III shows two additional formulations that have been used to successfully grow a number of cell lines using the fed-batch mode. The table shows the levels of the various compounds at the start of the culture cycle and later during the culture cycle after the concentrations of the compounds have been adjusted.

The formulations in columns 1 and 2, DM21 and DM21 with feed, respectively, were used to grow the hybridoma T88. Briefly, the fermentor (23 L working volume) was inoculated at approximately 100,000 viable cells per ml into basal medium DM21 with 8 mM L-glutamine. pH was controlled at 7.0 +/−0.05 by carbon dioxide gassing or NaOH addition. Dissolved oxygen was controlled at 20% +/−5% of air saturation. Temperature was controlled at 36.5 +/−0.3° C.

Nutrients were added to the culture in proportion to estimated viable cell density. Viable cell density was predicted from the oxygen sparge rate into the fermentor (an indicator of volumetric oxygen demand). Nutrients feeds 1 and 2 were added to the fermentor daily at a rate of 5 ml per day per $10^9$ viable cells. Glucose was added to 1 ml per day per $10^9$ viable cells.

Figure 7:
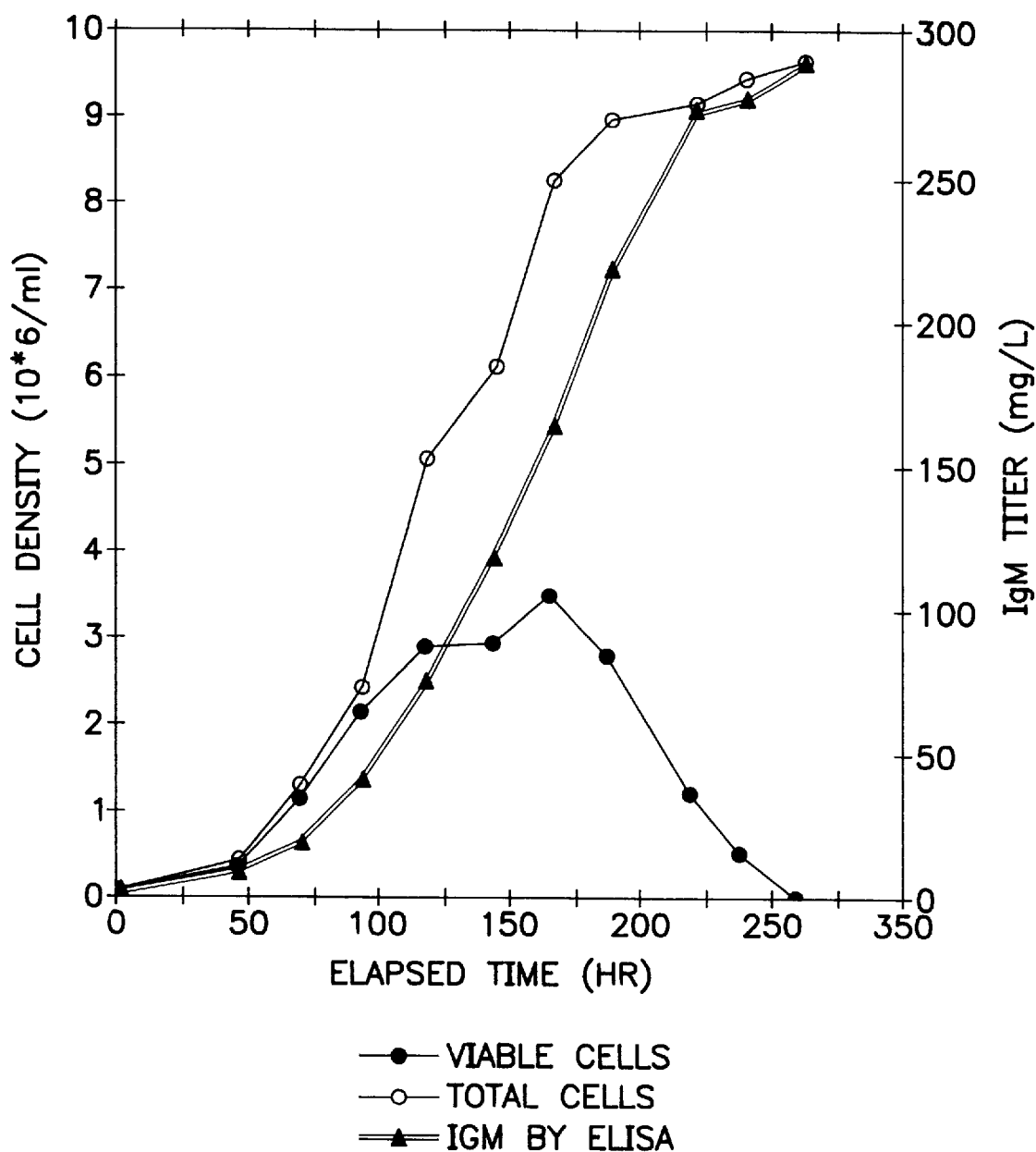
Figure 7 shows the effects of growing T88 in fed-batch mode using the formulations of Table III, columns 1 and 2.

FIG. 7 shows that viable cell density plateaus by about 175 hours of culture whereas antibody production and total cell number is increasing even past 250 hours. IgM levels at this time are about 300 mg/l.

TABLE III

| Component | (DM21) 1 (Start of Culture) (mg/l) | 2 (With Feeds) (mg/l) |
|---|---|---|
| Amino Acids | | |
| Arginine | 500.0 | 622.0 |
| Arginine.HCl | 42.0 | 38.6 |
| Asparagine | 178.4 | 571.8 |
| Aspartate | 60.0 | 381.1 |
| Cystine | 199.0 | 427.7 |
| Glutamate | 60.0 | 218.1 |
| Glutamine | 1168.0 | 3455.0 |
| Glycine | 70.0 | 227.3 |
| Histidine | 107.5 | 343.7 |
| Histadine.HCl.H$_2$O | 21.0 | 19.3 |
| Hydroxyproline | 10.0 | 9.2 |
| Isoleucine | 327.4 | 1116.7 |
| Leucine | 327.4 | 708.6 |
| Lysine.HCl | 343.1 | 967.0 |
| Methionine | 122.5 | 357.5 |
| Phenylalanine | 140.5 | 374.0 |
| Proline | 60.0 | 137.1 |
| Serine | 136.0 | 369.8 |
| Threonine | 207.6 | 353.6 |
| Tryptophan | 110.5 | 305.4 |
| Tyrosine.2Na.2H$_2$O | 216.0 | 851.3 |
| Valine | 206.8 | 842.8 |
| Vitamins | | |
| pAminobenzoic Acid | 0.5 | 2.1 |
| Biotin | 0.1 | 0.4 |
| CA Pantothenate | 2.1 | 8.9 |
| Folic Acid | 2.5 | 10.5 |
| Nicotinamide | 2.5 | 10.5 |
| Pyridoxal.HCl | 2.0 | 8.4 |
| Pyridoxine.HCl | 0.5 | 2.1 |
| Riboflavin | 0.3 | 1.1 |
| Thiamine.HCl | 2.5 | 10.5 |
| Vitamin B12 | 0.0025 | 3.3 |
| Salts | | |
| Ca (NO$_3$)$_2$.4H$_2$O | 50.0 | 45.9 |
| KCl | 400.0 | 367.2 |
| MgSO$_4$.7H$_2$O | 150.0 | 137.7 |
| NaCl | 5000.0 | 4590.0 |
| Carbon/Energy Source | | |
| Glucose | 5250.0 | 10941.5 |
| Na Pyruvate | 110.0 | 1896.0 |
| Lipid Precursors | | |
| Choline Chloride | 44.0 | 122.4 |
| Ethanolamine | 10.0 | 25.2 |
| Glycerol | 200.0 | 183.6 |
| Inositol | 41.0 | 70.6 |
| Trace Elements | | |
| FeCl$_3$.6H$_2$O | 2.7 | 6.9 |
| Fe(NO$_3$)$_3$.9H$_2$O | 0.050 | 0.046 |
| (NH$_4$)$_6$Mo$_7$O$_{24}$ | 0.10 | 0.25 |
| CoCl$_2$.6H$_2$O | 0.10 | 0.25 |
| CuCl$_2$.2H$_2$O | 0.10 | 0.25 |
| MnCl$_2$.4H$_2$O | 0.10 | 0.25 |
| ZnCl$_2$ | 0.10 | 0.25 |
| Na$_2$ScO$_3$ | 0.020 | 0.051 |
| Selenous Acid | 0.0050 | 0.0046 |
| Disulfide Exchange Reagents | | |
| Glutathione (Reduced) | 0.5 | 0.5 |
| Monothioglycerol | 1.0 | 9.0 |
| Proteins | | |
| Insulin | 5.0 | 4.6 |
| Transferrin | 5.0 | 4.6 |
| Shear Protective Agent | | |
| Pluronic Polyol F68 | 1000.0 | 918.0 |
| pH Buffers | | |
| NaOH | 60.0 | 865.0 |
| HCl | (adequate toadjustpHto) | |
| NaH$_2$PO$_4$.H$_2$O | 830.0 | 761.9 |
| Na$_2$HPO$_4$.7H$_2$O | 360.0 | 330.5 |
| NaHCO$_3$ | 2850.0 | 2616.3 |
| Na Citrate.H$_2$O | 294.1 | 750.0 |
| Hepes | 2979.0 | 2734.7 |
| Phenol Red | 10.0 | 9.2 |

TABLE IV

| Component | mg/l |
|---|---|
| Nutrient Feeds | |
| Feed 1 | |
| 1. ARGININE | 2000.0 |
| 2. ASPARTIC ACID | 4000.0 |
| 3. CYSTINE | 3000.0 |
| 4. GLUTAMIC ACID | 2000.0 |
| 5. GLYCINE | 2000.0 |
| 6. HISTIDINE | 3000.0 |
| 7. ISOLEUCINE | 10000.0 |

TABLE IV-continued

Nutrient Feeds

| Component | mg/l |
|---|---|
| 8. LEUCINE | 5000.0 |
| 9. LYSINCE.HCl | 8000.0 |
| 10. PHENYLALANINE | 3000.0 |
| 11. PROLINE | 1000.0 |
| 12. SERINE | 3000.0 |
| 13. THREONINE | 2000.0 |
| 14. TRYPTOPHAN | 2500.0 |
| 15. TYROSINE.2H$_2$0.2Na | 8000.0 |
| 16. VALINE | 8000.0 |
| 17. FOLIC ACID | 100.0 |
| 18. SODIUM CITRATE.2H$_2$0 | 5880.0 |
| 20. FeCl$_3$.6H$_2$O | 54.0 |
| 22. (NH$_4$)$_6$Mo$_7$O$_{24}$.4H$_2$O | 2.0 |
| 23. CoCl$_2$.6H$_2$O | 2.0 |
| 24. CuCl$_2$.2H$_2$O | 2.0 |
| 25. MnCl$_2$.4H$_2$O | 2.0 |
| 26. ZnCl$_2$ | 2.0 |
| 27. Na$_2$SeO$_3$ | 0.4 |
| 28. MONOTHIOGLYCEROL | 100.0 |
| 29. NaOH | 1200.0 |
| Feed 2 | |
| 1. ASPARAGINE | 5000 |
| 2. GLUTAMINE | 29200 |
| 3. METHIONINE | 3000 |
| 4. SODIUM PYRUVATE | 22000 |
| 5. ETHANOLAMINE | 200 |
| 6. CHOLINE CHLORIDE | 1000 |
| 7. INOSITOL | 400 |
| 8. pAMINOBENZOIC ACID | 20 |
| 9. BIOTIN | 4 |
| 10. PANTOTHENIC ACID (Ca) | 85 |
| 11. NICOTINAMIDE | 100 |
| 12. PYRIDOXAL | 80 |
| 13. PYRIDOXINE.HCl | 20 |
| 14. RIBOFLAVINE | 10 |
| 15. THIAMINE.HCl | 100 |
| 16. VITAMIN B12 | 40 |

EXAMPLE 8

Figure 8:
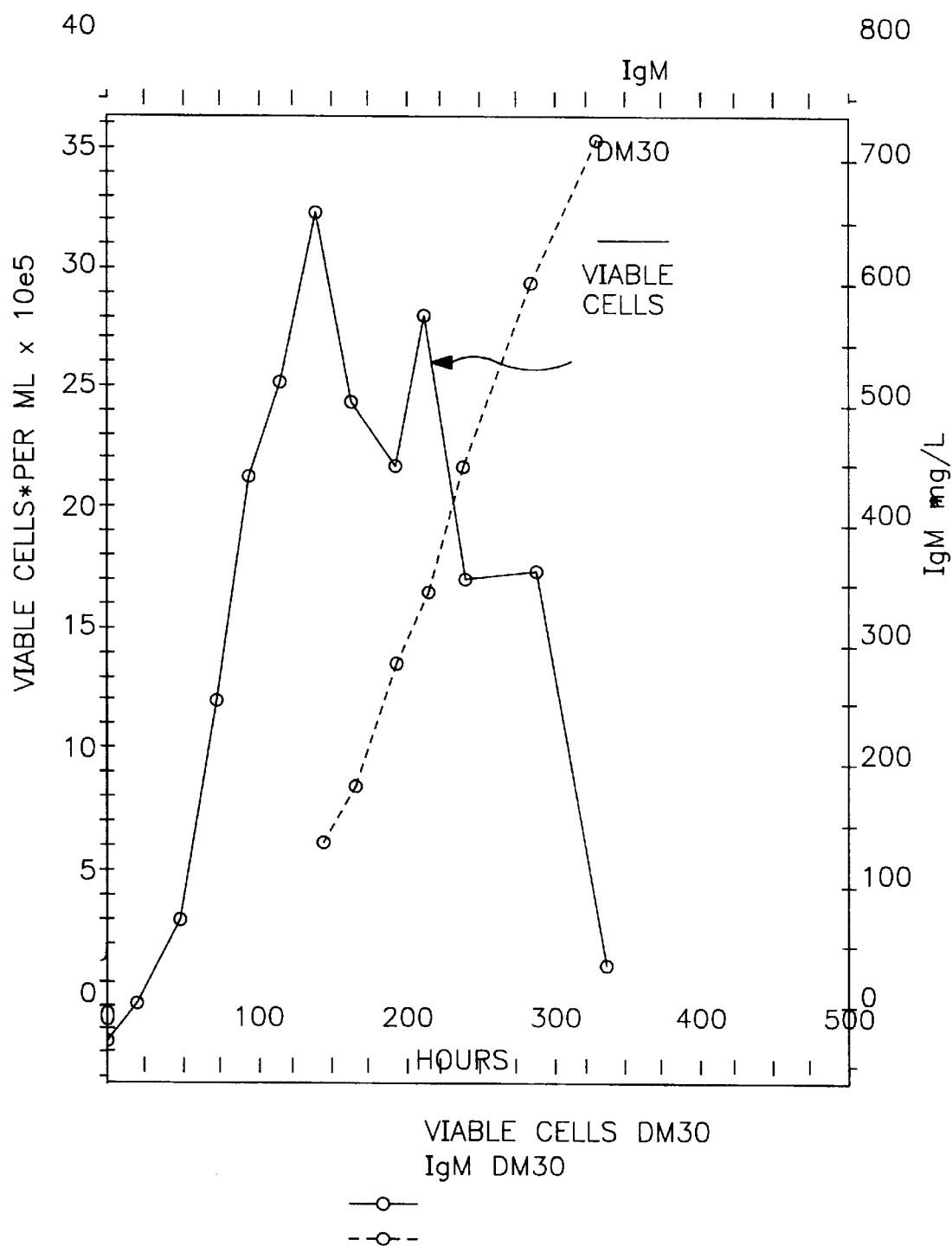
FIG. 8 shows the growth properties and levels of antibody produced by the hybridoma T88-151 in DM30 media supplemented with reagents of the Primary and Class I Supplements. Note that the media used in this experiment is devoid of insulin, selenous acid and transferrin and contains high levels of iron and citrate.

Table I, column 6, shows a protein free composition wherein standard medium has been supplemented with reagents of the Primary Supplement, as well as with the Class I reagent, monothioglycerol, to produce a medium termed DM30. Monothioglycerol was used at a concentration of 10 mg/l. This composition is devoid of insulin, selenous acid and transferrin, and has high levels of iron chloride and sodium citrate to compensate for the lack of these hormones. FIG. 8 shows that the levels of antibody obtained from the hybridoma T88 are in excess of 700 mg/l of IgM after about 330 hours of growth.

EXAMPLE 9

Figure 9:
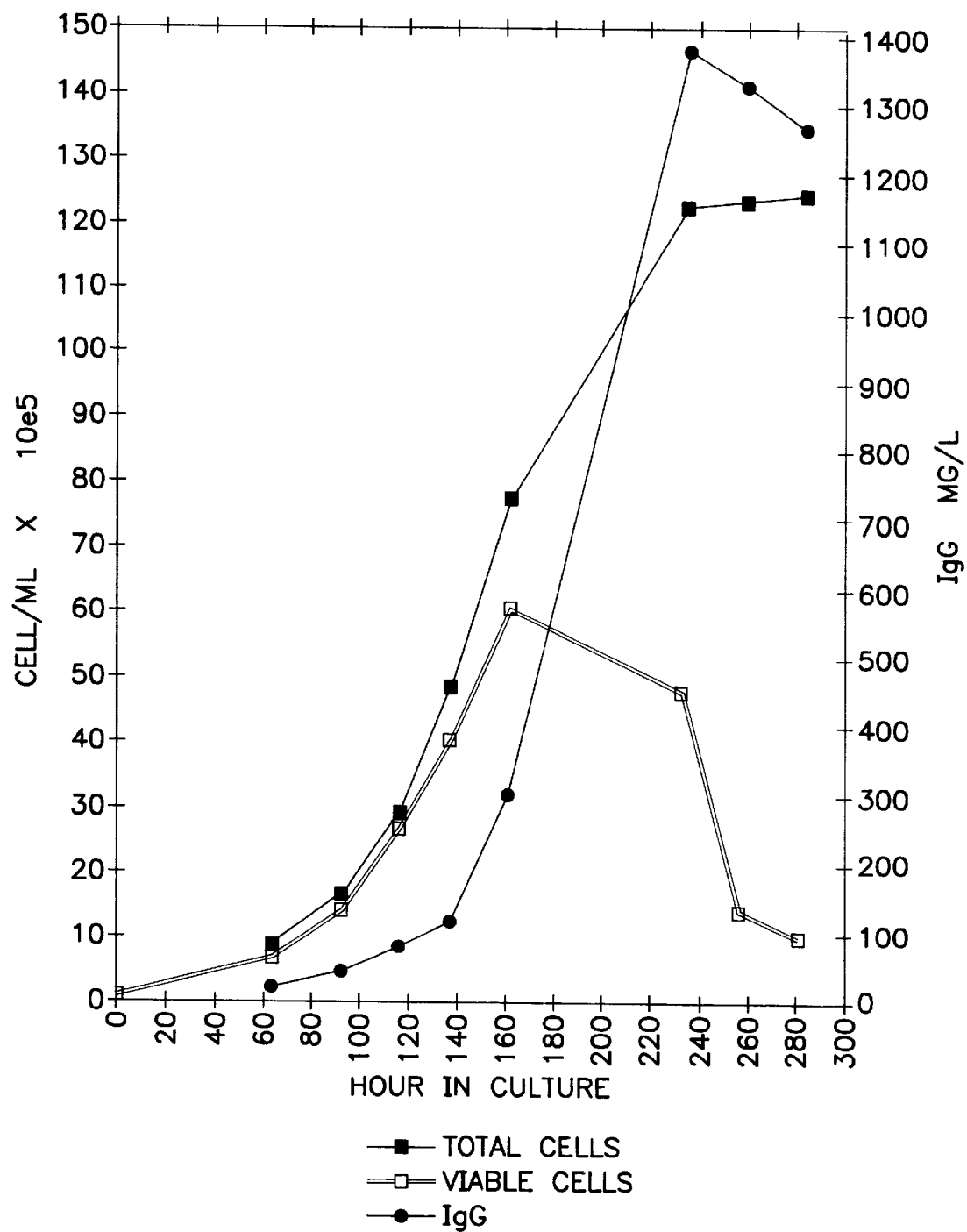
FIG. 9 shows the growth properties and levels of antibody produced by the hybridoma FB2, using the media of FIG. 8, but additionally containing insulin, selenous acid and transferrin.

Primary Supplement Plus Elevated Levels of Monothioglycerol And Insulin and Transferrin The DM30 composition used in Example 8, was supplemented with 5 mg/l of both insulin and transferrin, and 0.0050 mg/l of selenous acid, and the Class I reagent nicotinamide and employed here to test the cell growth and antibody producing effects on the cell line, FB2. FB2 is a murine hybridoma that secretes anti-phosphotyrosine monoclonal antibody. It is obtainable from Rusty Williams at the University of San Francisco, Calif. It is apparent from FIG. 9 that antibody levels produced by FB2 are in excess of 1.3 g/l, and this is attained after about 230 hours of culture. The maximum number of viable cells (6×10$^6$ vc/ml) is reached after about 160 hours of culture, while the maximum number of total cells (1.2×10$^7$ tc/ml) is achieved after about 240 hours.

In addition to the cell line FB2, two other cell lines were tested for growth and antibody production in DM30. The cell lines were KT3, a murine hybridoma, and 2B1 a murine quadroma. The maximum viable cell densities and antibody levels reached in DM30 are shown in Table V. KT3 and 2B1 exhibited 450 mg/L and 1200 mg/L of antibody, respectively.

TABLE V

| KT3 | Mu xMu IgG | 6.5 | 450 |
|---|---|---|---|
| 2B1* | Mu xMu xMu xMu Bispecific IgG | 3.5 | 1200 |

*2B1 is described in U.S. Serial No. 249,710 and has American Type Culture Collection Accession No. CRL10197.

EXAMPLE 10

Figure 10:
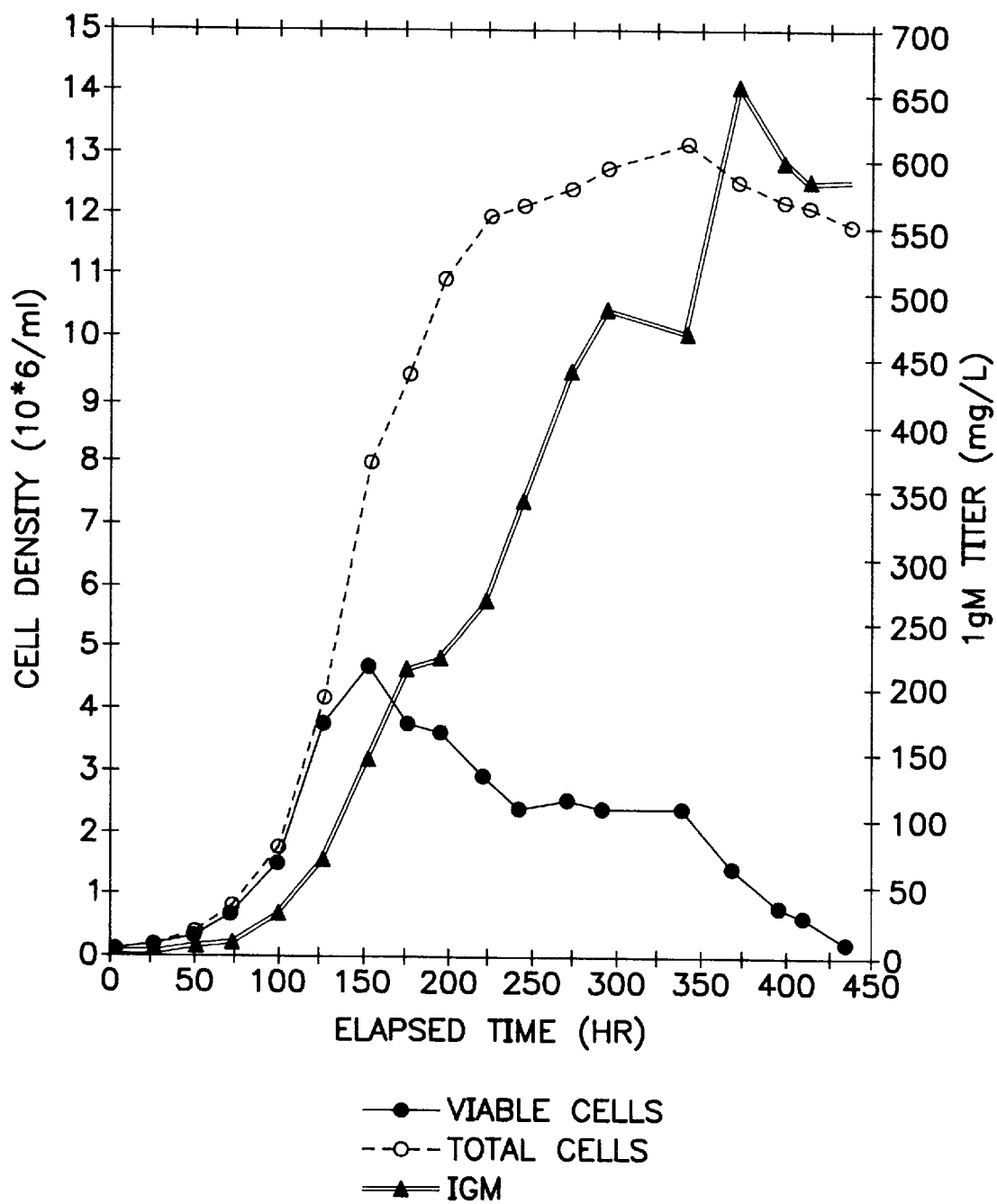
FIG. 10 shows the growth properties and levels of antibody produced by the hybridoma T88-151 in DM40.

Fed-Batch Using Primary Supplement/ Monothioglycerol No Insulin/Transferrin And Elevated Amounts of Asparagine and Nicotinamide The hybridoma T88-151 was grown in the medium shown in Table I, column 7. The medium is denoted DM40. The cells were grown in a 23 liter fermentor starting with an initial inoculum of 100,000 cells/ml. The initial glutamine concentration was 8 mM.

pH was controlled at 7.0+/−0.05 by carbon dioxide gassing or NaOH addition. Dissolved oxygen was controlled at 20%+/−5% of air saturation. Temperature was controlled at 36.5 +/−0.3 C. Cells were fed during the culture period with glucose and glutamine feeds from 250 g/L and 200 mm/L stock solutions, respectively. Glucose was added to the culture at 0.6 grams per day per 10$^9$ viable cells from 72–126 hours elapsed time, and at 0.2 grams per day per 10$^9$ viable cells from 126 hours to the end of culture (435 hours). Glutamine was added to the culture at 1.5 mmoles per day per 10$^9$ viable cells from 72–126 hours elapsed time, and at 0.5 mmoles per day per 10$^9$ viable cells from 126 hours to the end of culture (435 hours). FIG. 10 shows that viable cell density reaches a maximum of approximately 4.8 million per ml at 150 hours of culture. Total cell density continues to increase through 350 hours, where IgM titer reaches a maximum of approximately 600 mg/L.

EXAMPLE 11

Growth of Hybridoma KT3 in DM26 Primary Supplement/Class I Reagents

DM26 is a generic formulation that readily supports the growth of numerous cell lines. It lends itself to adjustments of the various reagents to produce media that is optimal for cell growth and product expression. Table VI shows the composition of DM26 with insulin, transferrin and selenous acid. These latter reagents, however, can be omitted if desired and substituted by Fe/citrate, as described in previous examples.

The formulation of DM26 was tested for cell growth and antibody production of the hybridoma cell line KT3. The cells were grown in Fed-Batch mode with an initial concentration of single glutamine that increased to 40 mg/L at the end of the culture period.

TABLE VI

DM26

| | mg/L | | mg/L |
|---|---|---|---|
| Sodium Chloride NaCl | 4300 | Nicotinic Acid Amide | 5 |
| Potassium Chloride KCl | 400 | Thiamine MCl | 5 |
| Glucose (Dextrose) anhyd | 5250 | Choline Chloride | 44 |
| L-Arginine HCl | 604.7 | Ferric Chloride $FeCl_3 \cdot 6H_2O$ | 2.7 |
| L-Asparagine $H_2O$ | 545.6 | Pyruvic Acid, Na salt | 110 |
| L-Aspartic Acid | 300 | Calcium Nitrate $Ca(NO_3)_2 \cdot 4H_2O$ | 50 |
| L-Glutamic Acid | 50 | Magnesium Sulfate, anhyd $MgSO_4$ | 73.26 |
| Glycine | 120 | Sodium Citrate $2H_2O$ | 294 |
| L-Histidine HCl $H_2O$ | 202.68 | Sodium Phosphate, dibasic | 190.66 |
| L-Isoleucine | 500 | $Na_2HPO_4$ anhyd | |
| L-Leucine | 600 | Sodium Phosphate, monobasic | 830 |
| L-Lysine HCl | 500 | $NaH_2PO_4 \cdot H_2O$ | |
| L-Methionine | 200 | HEPES, acid form | 2979 |
| L-Phenylalanine | 200 | p-Aminobenzoic Acid | 1 |
| L-Proline | 50 | d-Biotin | .2 |
| L-Serine | 250 | Glutathione, reduced | .5 |
| L-Threonine | 250 | Riboflavin | .6 |
| L-Tryptophan | 125 | Vitamin B12 | .005 |
| L-Tyrosine 2Na $2H_2O$ | 300 | Ammonium Molybdate $4H_2O$ | .3 |
| L-Valine | 400 | $(NH_4)_6Mo_7O_{24} \cdot 4H_2O$ | .3 |
| Phenol Red, Na salt | 10.65 | Cobalt Chloride $CoCl_2 \cdot 6H_2O$ | .3 |
| Inositol | 41 | Cupric Chloride $CuCl_2 \cdot 2H_2O$ | .3 |
| Pantothenic Acid, Ca salt | 4 | Manganous Chloride $MoCl_2 \cdot 4H_2O$ | .3 |
| Folic Acid | 5 | Sodium Selenite $Na_2SeO_3$ | .06 |
| Pyridoxine HCl | 4 | Zinc Chloride, anhyd | .3 |
| Pluronic polyol F68 | 1000 | Monothioglycerol | 10 |
| Ethanolamine | 10 | Insulin | 5 |
| Transferrin | 5 | Cystine | 300 |
| $NaHCO_3$ | 2850 | $NaHCO_3$ | 2850 |
| | | 8-mg/L glutamine (8–40) glucose | |

Having described what applicants believe their invention to be, it will be appreciated that the invention should not be construed as limited in any manner whatsoever other than by the scope by the appended claims.

We claim:

1. A method of growing cells, comprising the step of contacting said cells with a cell culture medium comprising the following components:

(a) a first reagent selected from the group consisting of glutamine, glutamate, and asparagine, said first reagent being present at a concentration of at least 8 mM;

(b) phospholipid precursors comprising at least choline and ethanolamine;

(c) tryptophan; and (d) an amino acid other than tryptophan and other than said first reagent of (a);

and wherein said components are at concentrations effective to increase culture longevity and product expression by maintaining said cells in a pseudo-stationary growth phase for about 100 hours or longer.

2. A method of growing cells, comprising the step of contacting said cells with a cell culture medium comprising:

| Component | Concentration (mg/L) |
|---|---|
| $Ca(NO_3)_2 \cdot 4H_2O$ | 40–50 |
| KCl | 400–560 |
| $MgSO_4$ | [73.5] 73.26–242.8 |
| NaCl | [5,300] 4300–6,000 |
| $NaH_2PO_4 \cdot H_2O$ | 625–[732] 830 |
| $Na_2HPO_4$ | [320.4] 190.66–400.5 |
| Glucose | [2,700] 1000–[4,800] 5250 |
| Glutathione | 0.4–0.5 |
| HEPES | 2383.2–2979 |
| Sodium pyruvate | 44–1155 |
| $NaHCO_3$ | 2350–2850 |
| p-Aminobenzoate | 0.464–1[.0] |
| Biotin | 0.1–0.2 |
| Calcium pantothenate | [0.170] 1.7–4.0 |
| Folic acid | 1.6[0]–[4.0] 5 |
| Nicotinamide | 2[.0]–5[.0] |
| Pyridoxine hydrochloride | 0.48–[1.0] 4 |
| Riboflavin | 0.256–0.6 |
| Thiamine hydrochloride | 2.016–5[.0] |
| Vitamin B12 | 0.0025–0.24 |
| Choline chloride | 22.8–[23.5] 75 |
| Inositol | [24.9] 24.88–[41.0] 50 |
| Ethanolamine | 0.8–[10.0] 20 |
| [Glycerol] | [0–200] |
| Glutamine | 1160–[1180] 5844 |
| PLURONIC ® polyol F68 | 1000 |
| [Transferrin] | [4.0–5.0] |
| [$Na_2SeO_3$] | [.004–.005] |
| [$FeCl_3$] | [0–1.6] |
| [$(NH_4)_6Mo_7O_{24} \cdot 4H_2O$] | [0–0.1] |
| $CoCl_2 \cdot 6H_2O$ | .005–[0.1] 0.4 |
| [$CuCl_2 \cdot 2H_2O$] | [0–0.1] |
| $MnCl_2 \cdot 4H_2O$ | .002–[0.1] 0.4 |
| [$ZnCl_2$] | [0–0.1] |
| [$FeSO_4 \cdot 7H_2O$] | [0–0.11] |
| [Monothioglycerol] | [0–10] |
| [Citrate] | [0–258] |
| Arginine | 194.1–794 |
| [Aspartate] Asparagine | 125–[280] 1400 |
| [Cystine] | [49–195] |
| Glutamic acid | 50–308 |
| Glycine | 38–[56] 250 |
| Histidine | 45.2–[120] 300 |
| Isoleucine | 145.2–[282] 1000 |

-continued

| Component | Concentration (mg/L) |
|---|---|
| Leucine | 95.2–[282] 1200 |
| Lysine hydrochloride | 153.7–[317] 1000 |
| Methionine | 52–[217.6] 400 |
| Phenylalanine | 70–[232] 400 |
| Proline | 50–108 |
| Serine | 52.4–[136] 400 |
| Threonine | 72.2–[194] 500 |
| Tryptophan | 19–[140] 250 |
| Tyrosine | 66.4–[158] 500 |
| Valine | 97–[191] 600 |

3. A method of growing cells, comprising the step of contacting said cells with a cell culture medium comprising the following components:
   (a) a first reagent selected from the group consisting of glutamine, glutamate, and asparagine, said first reagent being present at a concentration of at least 8 mM;
   (b) phospholipid precursors comprising at least choline and ethanolamine;
   (c) tryptophan; and
   (d) an amino acid other than tryptophan and other than said first reagent of (a); and wherein said components are at concentrations effective to increase product expression of said cells to about 470 mg per liter or more of final desired protein product yield at the end of cell culture.

4. A method of growing cells, comprising the step of contacting said cells with a cell culture medium comprising the following components at the concentration set forth:

| Component | Concentration (mg/L) |
|---|---|
| Choline chloride | >22.8 |
| Ethanolamine | >0.8 |
| Glutamine | >1160 |
| Tryptophan | >19 | and at least one amino acid selected from the group consisting of the following amino acids at the concentrations set forth:

| Amino Acid | Concentration (mg/L) |
|---|---|
| Arginine | ≧194.1 |
| Asparagine | ≧125 |
| Aspartate | ≧0 |
| Cystine or cysteine | ≧0 |
| Glutamic acid | ≧50 |
| Glycine | ≧38 |
| Histidine | ≧45.2 |
| Isoleucine | ≧145.2 |
| Leucine | ≧95.2 |
| Lysine hydrochloride | ≧153.7 |
| Methionine | ≧52 |
| Phenylalanine | ≧70 |
| Proline | ≧50 |
| Serine | ≧52.4 |
| Threonine | ≧72.2 |
| Tyrosine | ≧66.4 |
| Valine | ≧97 |

5. The method of claim 3 or 4 wherein the cell culture medium further comprises a Class I Reagent selected from the group consisting of the following components:
   (i) a reducing reagent;
   (ii) a metal ion;
   (iii) a metal chelator; and
   (iv) a vitamin.

6. The method of claim 3 wherein the desired protein product is an antibody.

7. The method according to claim 1, further comprising contacting said cells with a growth hormone or a growth factor.

8. The method according to claim 1 further comprising contacting said cells with a Pluronic® polyol.

9. The method according to claim 1, wherein said cells are antibody secreting cells.

10. The method according to claim 1, wherein choline is present at a concentration between about 4 mg/L and 75 mg/L.

11. The method according to claim 1, wherein ethanolamine is present at a concentration between about 1 mg/L and 20 mg/L.

12. The method according to claim 1, wherein said phospholipid precursors further comprise a composition selected from the group consisting of serine, inositol, glycerol, phosphoethanolamine, phosphocholine, phosphatidylethanolamine, and phosphatidylcholine.

13. The method according to claim 12, wherein said composition is selected from the group consisting of serine, inositol, and glycerol.

14. The method according to claim 1, wherein said product expression is about 470 mg/L or more of final protein product yield at the end of cell culture.

15. The method according to claim 1, wherein said pseudo-stationary growth phase is maintained for about 150 hours or more.

16. The method according to claim 1 wherein said cells in culture are in a protein-free medium.

17. The method according to claim 1, wherein said cells in culture are in a serum-free medium.

18. The method of claim 1 wherein the cell culture medium further comprises a Class I Reagent selected from the group consisting of the following components:
   (i) a reducing reagent;
   (ii) a metal ion;
   (iii) a metal chelator; and
   (iv) a vitamin.

19. The method according to claim 18, wherein said metal ion is selected from the group consisting of calcium, magnesium, molybdenum, cobalt, copper, manganese, zinc, selenium, iron and combinations thereof.

20. The method according to claim 18 or 19, further comprising an amino acid selected from the group consisting of at least about 194 mg/L arginine, at least about 125 mg/L aspartate, at least about 49 mg/L cystine, at least about 38 mg/L glycine, at least about 50 mg/L glutamate, at least about 45.2 mg/L histidine, at least about 145.2 mg/L isoleucine, at least about 95.2 mg/L leucine, at least about 153.7 mg/L lysine, at least about 52 mg/L methionine, at least about 70 mg/L phenylalanine, at least about 50 mg/L proline, at least about 52.4 mg/L serine, at least about 72.2 mg/L threonine, at least about 19 mg/L tryptophan, at least about 66.4 mg/L tyrosine, and at least about 97 mg/L valine.

21. The method according to claim 18, wherein said reducing agent is monothioglycerol.

22. The method according to claim 21, wherein said reducing agent is included at a concentration between about 0.1 mg/L and 100 mg/L.

23. The method according to claim 18, wherein said metal chelator is selected from the group consisting of transferrin, ferritin, albumin, pyridoxyl isonicotinoyl hydrazone, choline citrate, and citrate.

24. The method according to claim 23, wherein said metal chelator is citrate.

25. The method according to claim 18, wherein said vitamin is selected from the group consisting of ascorbic acid, biotin, flavin adenine dinucleotide, folic acid, folinic acid, nicotinamide, p-amino-benzoic acid, pantothenate, pyridoxine, riboflavin, thiamine, vitamin B12 and combinations thereof.

26. A kit for prolonging the pseudo-stationary growth phase of cells grown in culture, comprising:
   (a) a first reagent selected from the group consisting of glutamine, glutamate, and asparagine, said first reagent providing a concentration of at least 5 mM;
   (b) phospholipid precursors comprising at least choline and ethanolamine;
   (c) tryptophan; and
   (d) an essential amino acid for growth of said cells other than tryptophan and other than said first reagent of (a); and
   wherein said components are at concentrations effective to increase culture longevity and product expression by maintaining said cells in a pseudo-stationary growth phase for about 100 hours or longer.

27. The kit according to claim 26, wherein the concentration of glutamine or glutamate is between 8 and 20 mM.

28. The kit according to claim 26 or 27, wherein the concentration of choline is between 4 and 75 mg/L.

29. The kit according to claim 26, wherein the concentration of ethanolamine is between 1 and 20 mg/L.

30. The kit according to claim 26 further comprising Class I reagents, wherein said Class I reagents comprise:
   (a) a reducing agent;
   (b) a metal ion;
   (c) a metal chelator; and
   (d) a vitamin;
and further wherein said Class I reagents are at concentrations effective to maintain said cells for a prolonged time in a pseudo-stationary growth phase.

31. The kit according to claim 30, wherein said metal ion is selected from the group consisting of calcium, cobalt, copper, iron, magnesium, manganese, molybdenum, selenium and zinc.

32. The kit according to claim 30, further comprising an amino acid selected from the group consisting of at least about 426 mg/L arginine, at least about 75 mg/L aspartate, at least about 147 mg/L cystine, at least about 60 mg/L glycine, at least about 30 mg/L glutamate, at least about 84 mg/L histidine, at least about 234 mg/L isoleucine, at least about 234 mg/L leucine, at least about 279 mg/L lysine, at least about 66 mg/L methionine, at least about 120 mg/L phenylalanine, at least about 30 mg/L proline, at least about 108 mg/L serine, at least about 174 mg/L threonine, at least about 30 mg/L tryptophan, at least about 138 mg/L tyrosine, and at least about 171 mg/L valine.

33. The kit according to claim 30, wherein said reducing agent is monothioglycerol.

34. The kit according to claim 30, wherein said metal chelator is selected from the group consisting of transferrin, ferritin, albumin, pyridoxyl isonicotinoyl hydrazone, choline citrate, and citrate.

35. The kit according to claim 30, wherein said vitamin is selected from the group consisting of ascorbic acid, biotin, flavin adenine dinucleotide, folic acid, folinic acid, nicotinamide, p-amino-benzoic acid, pantothenate, pyridoxine, riboflavin, thiamine, and vitamin B12.

36. A method of growing cells, comprising the step of contacting said cells with a cell culture medium comprising:

| Component | Concentration (mg/L) |
| --- | --- |
| $Ca(NO_3)_2 \cdot 4H_2O$ | 35–55 |
| KCl | 350–600 |
| $MgSO_4$ | 70–250 |
| NaCl | 3700–6100 |
| $NaH_2PO_4 \cdot H_2O$ | 600–900 |
| $Na_2HPO_4$ | 180–450 |
| Glucose | 900–5300 |
| Glutathione | 0.3–0.6 |
| HEPES | 2300–2990 |
| Sodium pyruvate | 40–1120 |
| $NaHCO_3$ | 2340–2900 |
| p-Aminobenzoate | 0.40–1.50 |
| Biotin | 0.05–0.3 |
| Calcium pantothenate | 1.50–4.50 |
| Folic acid | 1.0–5.5 |
| Nicotinamide | 1.5–6.0 |
| Pyridoxine hydrochloride | 0.4–4.5 |
| Riboflavin | 0.20–0.70 |
| Thiamine hydrochloride | 2.4–5.5 |
| Vitamin B12 | 0.0020–0.30 |
| Choline chloride | 10–80 |
| Inositol | 23–55 |
| Ethanolamine | 0.7–25 |
| Glutamine | 1160–6700 |
| Pluronic ® polyol F68 | 800–1200 |
| $(NH_4)_6Mo_7O_{24} \cdot 4H_2O$ | 0.003–0.5 |
| $CoCl_2 \cdot 6H_2O$ | 0.005–0.5 |
| $CuCl_2 \cdot 2H_2O$ | 0.01–0.5 |
| $MnCl_2 \cdot 4H_2O$ | 0.01–0.5 |
| $ZnCl_2$ | 0.003–0.5 |
| Monothioglycerol | 0.7–12 |
| Citrate | 1–300 |
| Arginine | 190–1420 |
| Glutamic acid | 45–350 |
| Glycine | 30–300 |
| Histidine | 50–350 |
| Isoleucine | 1040–1050 |
| Leucine | 150–1250 |
| Lysine hydrochloride | 145–1050 |
| Methionine | 50–450 |
| Phenylalanine | 65–450 |
| Proline | 45–150 |
| Serine | 50–450 |
| Threonine | 70–600 |
| Tryptophan | 18–320 |
| Tyrosine | 60–550 |
| Valine | 90–650 |

37. The method according to claim 18, 19, 23, 25 2, 36, 1 or 3, wherein said first reagent is glutamine and further wherein said glutamine is present at a concentration between about 8 mM and 40 mM.

38. The method according to claim 18, 19, 23, 25, 2, 36, 1, 3 or 4, wherein said cells are hybridomas.

39. The method according to claim 18, 19, 23, 25, 2, 36, 1, 4 or 4, wherein said cells are human cells.

* * * * *